(12) United States Patent
Piletz et al.

(10) Patent No.: US 6,576,742 B1
(45) Date of Patent: *Jun. 10, 2003

(54) DNA SEQUENCE ENCODING A HUMAN IMIDAZOLINE RECEPTOR AND METHOD FOR CLONING THE SAME

(75) Inventors: John E. Piletz, Madison, MS (US); Tina R. Ivanov, Jackson, MS (US)

(73) Assignee: The University of Mississippi Medical Center, Jackson, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/389,487

(22) Filed: Sep. 3, 1999

Related U.S. Application Data

(62) Division of application No. 08/650,766, filed on May 20, 1996, now Pat. No. 6,015,690.
(60) Provisional application No. 60/012,600, filed on Mar. 1, 1996.

(51) Int. Cl.$^7$ .............................................. C07K 14/705
(52) U.S. Cl. ...................... 530/350; 536/23.5; 435/69.1
(58) Field of Search ........................ 530/350; 536/23.5; 435/69.1

(56) References Cited

U.S. PATENT DOCUMENTS 5,556,753 A * 9/1996 Bard .............................. 435/6
6,033,871 A * 3/2000 Piletz ........................ 435/69.1

OTHER PUBLICATIONS

Wang et al., Molecular Pharmacology 43 (4) 509–515, Apr. 1993.*
Lin et al., Science 190:61–63, Oct. 1975.*
P. Ernsberger et al., "Role of Imidazole Receptors in the Vasodepressor Response to Clonidine Analogs in the Rostral Ventrolateral Medulla$^1$", The Journal of Pharmacology and Experimental Therapeutics vol. 253, No. 1, pp. 408–418, (1990).
J. Piletz et al., "Nonadrenergic Imidazoline Binding Sites on Human Platelets", The Journal of Pharmacology and Experimental Therapeutics, vol. 267, No. 3, pp. 1493–1502, (1993).
B. Lanier et al., "Structral and Ligand Recognition Properties of Imidazoline Binding Proteins in Tissues of Rat and Rabbit", The American Society for Pharmacology and Experimental Therapeutics, vol. 48, pp. 703–710, (1995).
F. Bennai et al., "Antiidiotypic Antibodies as Tools to Study Imidazoline Receptors", Annals New York Academy of Sciences, vol. 763, pp. 140–148, (1995).
H. Wang et al., "Isolation and Characterization of Imidazoline Receptor Protein from Bovine Adrenal Chromaffin Cells", The American Society for Pharmacology and Experimental Therapeutics, vol. 42, pp. 792–801, (1992).
H. Wang et al., "Production and Characterization of Antibodies Specific for the Imidazoline Receptor Protein", The American Society for Pharmacology and Experimental Therapeutics, vol. 43, pp. 509–515, (1993).
P. Ernsberger et al., "I$^1$–Imidazoline Receptors Definition, Characterization, Distribution, and Transmembrane Signaling$^a$", Annals New York Academy of Sciences, vol. 763, pp. 22–42, (1995).
Fourth IBRO World Congress of Neuroscience. Abstract G2.29, Piletz et al. Platelet a$^2$– and 1$^1$ –Imidizoline Binding Sites in Depression, Kyoto, Japan, Jul. 9–14 (1995).
J. Piletz et al., "Imidazoline Receptors in Depression", American College of Neuropsychopharmacology, 34th Annual Meeting, Poster Session 1, p. 119, (1995).
A. Parini et al., "The Elusive Family of Imidazoline Binding Sites", TiPS, vol. 17, pp. 13–16, (1996).
J. Piletz et al., "Desipramine Lowers Tritiated Para–Aminoclonidine Binding in Platelets of Depressed Patients", Arch Gen Psychiatry, vol. 48, pp. 813–820, (1991).
J. Piletz et al., "Psychopharmacology of Imidazoline and a$_2$–Adrenergic Receptors: Implications for Depression", Critical Reviews in Neurobiology, vol. 9, No. 1, pp. 29–66, (1994).
Adams et al., EST04033 Homo sapiens cDNA, locus TO6144, Jun. 30, 1993.*

* cited by examiner

Primary Examiner—Lorraine Spector
Assistant Examiner—Eliane Lazar-Wesley
(74) Attorney, Agent, or Firm—Crowell & Moring LLP

(57) ABSTRACT

A cDNA encoding a human imidazoline receptor is described. The amino acid sequence of the entire imidazoline receptor protein is identified, as well as a C-terminal fragment believed to contain the imidazoline binding site of the receptor. The protein is highly unique in its sequence and may represent the first in a novel family of receptor proteins. Methods of cloning the cDNA and expressing the imidazoline receptor in a host cell are described. Also, a screening method for identifying drugs that interact with the imidazoline receptor is described.

8 Claims, 3 Drawing Sheets

HIPPOCAMPUS
1   2

NRL
1   2

REIS AB
1:15,000 DILUTION

DONTEWILL AB
1:20,000 DILUTION

SEQUENCE LISTING

<160> NUMBER OF SEQ ID NOS: 21

<210> SEQ ID NO 1
<211> LENGTH: 3385
<212> TYPE: DNA
<213> ORGANISM: Homo sapiens
<220> FEATURE:
<221> NAME/KEY: CDS
<222> LOCATION: (1398)..(3383)

<400> SEQUENCE: 1

```
gctctagaac tagtggatcc cccgggctgc aggaattcca gtttaatact aaccctaatg      60
tgtgactgcg gtttacaaag agctctgtat cacctgggat agctttcagt agcaattcac     120
tacaactggt cctaaaaaat aataacaata ataataataa ttagagaatt aaaacccaac     180
agcatgttga atggttaaaa tcacgtaaga actgaaattt ggggtggggg tgtcctcaac     240
agctgagctt gtcctagcag tgaaaatgct cgcctccaag cagggctcag aaaggtctgg     300
agccctccag gcagagggct gagctcaggg ggctcttgga ggacactcac cccatggtcc     360
atgggatgct tctggcttcc ttaaaaacag ttgggcatcc gcattgtata agtaggtgga     420
gaccctagtg tggttctttt gaaggatatg ggaagggagg atgacgaact agagaagtgg     480
gaggggacca aaatcactga ggtcccagaa tatcatagat ttgggtatag gattggggtc     540
actaagaatt gagcaccagg aattccagct tcttcccatt aaagaaactg ggactggttt     600
tgccttggag gcctatgtag tgttttctgc ccctgtccca taccaagtct cattgatatt     660
tctgcagaat atcagatgaa aatctatttc taaagaccat tgggagaatg ggtggtggag     720
aaggagttgg agtggggttg gggggcagtt aaaaatgaat aaaaatctct cagctacaga     780
acccaaacat cacttccctc cgcattcaca gcatttccca gcagtcccca gatggttgtt     840
tccgtgggga cacagcagct gcctcatttc ccttcaggcc ccatgggctg ctggtcaacc     900
tcaggatcta ctaaagatga cgcaaatgcc gactgaacaa tctgaaaccc aaaggactcg     960
aggagagaca tgttctgctg aggagagaaa ggtgagccaa gggcagggcc caggtccccc    1020
aggggccccc cgagagcccg gacatgcacc ttctggatgt gtttgttcaa gtaggactta    1080
gagcggaaga agctcccaca ttcagggcat gggtacttct tctccccatc agactccatt    1140
ttgtttttgg ggactgccat gtcgcaggag aaagagccat tggcactctg cttctctggc    1200
gtcttcaggt cgctggcatc tgagaggtca ccataggagt cagagctctc aatcggatcc    1260
tgatgtgagc atttctggcc ttctcggtta cagatactgc agaagttgct gggcccctcg    1320
ctgtgcttct tcaggtggtc tgccatgtat gctgcccgca agtacttccc acacacctgg    1380
cagggcacct tgtcttc atg aca ggc cag gtg gga gcg cag acg gtc tcg         1430
                   Met Thr Gly Gln Val Gly Ala Gln Thr Val Ser
                    1               5                  10 ggt ggc aaa aga agc att gca ggt ctg aca ctt gtg agg ccg ctc aga       1478
Gly Gly Lys Arg Ser Ile Ala Gly Leu Thr Leu Val Arg Pro Leu Arg
         15                  20                  25
```

-continued

| | |
|---|---|
| agt gtg cac ctg ctt gat atg tcc gtt caa gtg atc agg cct gga gaa<br>Ser Val His Leu Leu Asp Met Ser Val Gln Val Ile Arg Pro Gly Glu<br>         30                     35                     40 | 1526 |
| gcc ttt ccc aca gct ctg gca gat gta agg cgg aat tcc cca gag aag<br>Ala Phe Pro Thr Ala Leu Ala Asp Val Arg Arg Asn Ser Pro Glu Lys<br>         45                     50                     55 | 1574 |
| aag ggt ggt gaa gac tcc cgg ctc tca gct gcc ccc tgc atc aga ccc<br>Lys Gly Gly Glu Asp Ser Arg Leu Ser Ala Ala Pro Cys Ile Arg Pro<br>60                   65                     70                     75 | 1622 |
| agc agc tcc cct ccc act gtg gct ccc gca tct gcc tcc ctg ccc cag<br>Ser Ser Ser Pro Pro Thr Val Ala Pro Ala Ser Ala Ser Leu Pro Gln<br>                   80                     85                     90 | 1670 |
| ccc atc ctc tct aac caa gga atc atg ttc gtt cag gag gag gcc ctg<br>Pro Ile Leu Ser Asn Gln Gly Ile Met Phe Val Gln Glu Glu Ala Leu<br>         95                     100                    105 | 1718 |
| gcc agc agc ctc tcg tcc act gac agt ctg act ccc gag cac cag ccc<br>Ala Ser Ser Leu Ser Ser Thr Asp Ser Leu Thr Pro Glu His Gln Pro<br>               110                    115                    120 | 1766 |
| att gcc cag gga tgt tct gat tcc ttg gag tcc atc cct gcg gga cag<br>Ile Ala Gln Gly Cys Ser Asp Ser Leu Glu Ser Ile Pro Ala Gly Gln<br>125                    130                    135 | 1814 |
| gca gct tcc gat gat tta agg gac gtg cca gga gct gtt ggt ggt gca<br>Ala Ala Ser Asp Asp Leu Arg Asp Val Pro Gly Ala Val Gly Gly Ala<br>140                   145                    150                   155 | 1862 |
| agc cca gaa cat gcc gag ccg gag gtc cag gtg gtg ccg ggg tct ggc<br>Ser Pro Glu His Ala Glu Pro Glu Val Gln Val Val Pro Gly Ser Gly<br>               160                    165                    170 | 1910 |
| cag atc atc ttc ctg ccc ttc acc tgc att ggc tac acg gcc acc aat<br>Gln Ile Ile Phe Leu Pro Phe Thr Cys Ile Gly Tyr Thr Ala Thr Asn<br>               175                    180                    185 | 1958 |
| cag gac ttc atc cag cgc ctg agc aca ctg atc cgg cag gcc atc gag<br>Gln Asp Phe Ile Gln Arg Leu Ser Thr Leu Ile Arg Gln Ala Ile Glu<br>               190                    195                    200 | 2006 |
| cgg cag ctg cct gcc tgg atc gag gct gcc aac cag cgg gag gag ggc<br>Arg Gln Leu Pro Ala Trp Ile Glu Ala Ala Asn Gln Arg Glu Glu Gly<br>205                    210                    215 | 2054 |
| cag ggt gaa cag ggc gag gag gag gat gag gag gag gaa gag gag<br>Gln Gly Glu Gln Gly Glu Glu Glu Asp Glu Glu Glu Glu Glu Glu<br>220                    225                    230                    235 | 2102 |
| gac gtg gct gag aac cgc tac ttt gaa atg ggg ccc cca gac gtg gag<br>Asp Val Ala Glu Asn Arg Tyr Phe Glu Met Gly Pro Pro Asp Val Glu<br>               240                    245                    250 | 2150 |
| gag gag gag gga gga ggc cag ggg gag gaa gag gag gaa gag gag<br>Glu Glu Glu Gly Gly Gly Gln Gly Glu Glu Glu Glu Glu Glu Glu<br>               255                    260                    265 | 2198 |
| gat gaa gag gcc gag gag gag cgc ctg gct ctg gaa tgg gcc ctg ggc<br>Asp Glu Glu Ala Glu Glu Glu Arg Leu Ala Leu Glu Trp Ala Leu Gly<br>               270                    275                    280 | 2246 |
| gcg gac gag gac ttc ctg ctg gag cac atc cgc atc ctc aag gtg ctg<br>Ala Asp Glu Asp Phe Leu Leu Glu His Ile Arg Ile Leu Lys Val Leu<br>285                      290                    295 | 2294 |
| tgg tgc ttc ctg atc cat gtg cag ggc agt atc cgc cag ttc gcc gcc<br>Trp Cys Phe Leu Ile His Val Gln Gly Ser Ile Arg Gln Phe Ala Ala<br>300                      305                    310                    315 | 2342 |
| tgc ctt gtg ctc acc gac ttc ggc atc gca gtc ttc gag atc ccg cac<br>Cys Leu Val Leu Thr Asp Phe Gly Ile Ala Val Phe Glu Ile Pro His<br>               320                    325                    330 | 2390 |
| cag gag tct cgg ggc agc agc cag cac atc ctc tcc tcc ctg cgc ttt<br>Gln Glu Ser Arg Gly Ser Ser Gln His Ile Leu Ser Ser Leu Arg Phe<br>               335                    340                    345 | 2438 |

```
gtc ttt tgc ttc ccg cat ggc gac ctc acc gag ttt ggc ttc ctc atg       2486
Val Phe Cys Phe Pro His Gly Asp Leu Thr Glu Phe Gly Phe Leu Met
        350                 355                 360 ccg gag ctg tgt ctg gtg ctc aag gta cgg cac agt gag aac acg ctc       2534
Pro Glu Leu Cys Leu Val Leu Lys Val Arg His Ser Glu Asn Thr Leu
365                 370                 375 ttc att atc tcg gac gcc gcc aac ctg cac gag ttc cac gcg gac ctg       2582
Phe Ile Ile Ser Asp Ala Ala Asn Leu His Glu Phe His Ala Asp Leu
380                 385                 390                 395 cgc tca tgc ttt gca ccc cag cac atg gcc atg ctg tgt agc ccc atc       2630
Arg Ser Cys Phe Ala Pro Gln His Met Ala Met Leu Cys Ser Pro Ile
            400                 405                 410 ctc tac ggc agc cac acc agc ctg cag gag ttc ctg cgc cag ctg ctc       2678
Leu Tyr Gly Ser His Thr Ser Leu Gln Glu Phe Leu Arg Gln Leu Leu
        415                 420                 425 acc ttc tac aag gtg gct ggc ggc tgc cag gag cgc agc cag ggc tgc       2726
Thr Phe Tyr Lys Val Ala Gly Gly Cys Gln Glu Arg Ser Gln Gly Cys
        430                 435                 440 ttc ccc gtc tac ctg gtc tac agt gac aag cgc atg gtg cag acg gcc       2774
Phe Pro Val Tyr Leu Val Tyr Ser Asp Lys Arg Met Val Gln Thr Ala
445                 450                 455 gcc ggg gac tac tca ggc aac atc gag tgg gcc agc tgc aca ctc tgt       2822
Ala Gly Asp Tyr Ser Gly Asn Ile Glu Trp Ala Ser Cys Thr Leu Cys
460                 465                 470                 475 tca gcc gtg cgg cgc tcc tgc tgc gcg ccc tct gag gcc gtc aag tcc       2870
Ser Ala Val Arg Arg Ser Cys Cys Ala Pro Ser Glu Ala Val Lys Ser
            480                 485                 490 gcc gcc atc ccc tac tgg ctg ttg ctc acg ccc cag cac ctc aac gtc       2918
Ala Ala Ile Pro Tyr Trp Leu Leu Leu Thr Pro Gln His Leu Asn Val
        495                 500                 505 atc aag gcc gac ttc aac ccc atg ccc aac cgt ggc acc cac aac tgt       2966
Ile Lys Ala Asp Phe Asn Pro Met Pro Asn Arg Gly Thr His Asn Cys
        510                 515                 520 cgc aac cgc aac agc ttc aag ctc agc cgt gtg ccg ctc tcc acc gtg       3014
Arg Asn Arg Asn Ser Phe Lys Leu Ser Arg Val Pro Leu Ser Thr Val
525                 530                 535 ctg ctg gac ccc aca cgc agc tgt acc cag cct cgg ggc gcc ttt gct       3062
Leu Leu Asp Pro Thr Arg Ser Cys Thr Gln Pro Arg Gly Ala Phe Ala
540                 545                 550                 555 gat ggc cac gtg cta gag ctg ctc gtg ggg tac cgc ttt gtc act gcc       3110
Asp Gly His Val Leu Glu Leu Leu Val Gly Tyr Arg Phe Val Thr Ala
            560                 565                 570 atc ttc gtg ctg ccc cac gag aag ttc cac ttc ctg cgc gtc tac aac       3158
Ile Phe Val Leu Pro His Glu Lys Phe His Phe Leu Arg Val Tyr Asn
        575                 580                 585 cag ctg cgg gcc tcg ctg cag gac ctg aag act gtg gtc atc gcc aag       3206
Gln Leu Arg Ala Ser Leu Gln Asp Leu Lys Thr Val Val Ile Ala Lys
        590                 595                 600 acc ccc ggg acg gga ggc agc ccc cag ggc tcc ttt gcg gat ggc cag       3254
Thr Pro Gly Thr Gly Gly Ser Pro Gln Gly Ser Phe Ala Asp Gly Gln
605                 610                 615 cct gcc gag cgc agg gcc agc aat gac cag cgt ccc cag gag gtc cca       3302
Pro Ala Glu Arg Arg Ala Ser Asn Asp Gln Arg Pro Gln Glu Val Pro
620                 625                 630                 635 gca gag gct ctg gcc ccg gcc cca gtg gaa gtc cca gct cca gcc ccg       3350
Ala Glu Ala Leu Ala Pro Ala Pro Val Glu Val Pro Ala Pro Ala Pro
            640                 645                 650 gaa ttc gat atc aag ctt atc gat acc gtc gac ct                        3385
Glu Phe Asp Ile Lys Leu Ile Asp Thr Val Asp
        655                 660
```

<210> SEQ ID NO 2
<211> LENGTH: 1678
<212> TYPE: DNA
<213> ORGANISM: Homo sapiens

<400> SEQUENCE: 2

| | | | | | |
|---|---|---|---|---|---|
| atgacaggcc | aggtgggagc | gcagacggtc | tcgggtggca | aaagaagcat | tgcaggtctg | 60 |
| acacttgtga | ggccgctcag | aagtgtgcac | ctgcttgata | tgtccgttca | agtgatcagg | 120 |
| cctggagaag | cctttcccac | agctctggca | gatgtaaggc | ggaattcccc | agagaagaag | 180 |
| ggtggtgaag | actcccggct | ctcagctgcc | ccctgcatca | gacccagcag | ctcccctccc | 240 |
| actgtggctc | ccgcatctgc | ctccctgccc | cagcccatcc | tctctaacca | aggaatcatg | 300 |
| ttcgttcagg | aggaggccct | ggccagcagc | ctctcgtcca | ctgacagtct | gactcccgag | 360 |
| caccagccca | ttgcccaggg | atgttctgat | tccttggagt | ccatccctgc | gggacaggca | 420 |
| gcttccgatg | atttaaggga | cgtgccagga | gctgttggtg | gtgcaagccc | agaacatgcc | 480 |
| gagccggagg | tccaggtggt | gccggggtct | ggccagatca | tcttcctgcc | cttcacctgc | 540 |
| attggctaca | cggccaccaa | tcaggacttc | atccagcgcc | tgagcacact | gatccggcag | 600 |
| gccatcgagc | ggcagctgcc | tgcctggatc | gaggctgcca | ccagcgggga | ggagggccag | 660 |
| ggtgaacagg | gcgaggagga | ggatgaggag | gaggaagaag | aggaggacgt | ggctgagaac | 720 |
| cgctactttg | aaatggggcc | cccagacgtg | gaggaggagg | agggaggagg | ccaggggag | 780 |
| gaagaggagg | aggaagagga | ggatgaagag | gccgaggagg | agcgcctggc | tctggaatgg | 840 |
| gccctgggcg | cggacgagga | cttcctgctg | gagcacatcc | gcatcctcaa | ggtgctgtgg | 900 |
| tgcttcctga | tccatgtgca | gggcagtatc | cgccagttcg | ccgcctgcct | tgtgctcacc | 960 |
| gacttcggca | tcgcagtctt | cgagatcccg | caccaggagt | ctcggggcag | cagccagcac | 1020 |
| atcctctcct | ccctgcgctt | tgtcttttgc | ttcccgcatg | gcgacctcac | cgagtttggc | 1080 |
| ttcctcatgc | cggagctgtg | tctggtgctc | aaggtacggc | acagtgagaa | cacgctcttc | 1140 |
| attatctcgg | acgccgccaa | cctgcacgag | ttccacgcgg | acctgcgctc | atgctttgca | 1200 |
| ccccagcaca | tggccatgct | gtgtagcccc | atcctctacg | gcagccacac | cagcctgcag | 1260 |
| gagttcctgc | gccagctgct | caccttctac | aaggtggctg | gcggctgcca | ggagcgcagc | 1320 |
| cagggctgct | tccccgtcta | cctggtctac | agtgacaagc | gcatggtgca | gacggccgcc | 1380 |
| ggggactact | caggcaacat | cgagtgggcc | agctgcacac | tctgttcagc | cgtgcgcgc | 1440 |
| tcctgctgcg | cgccctctga | ggccgtcaag | tccgccgcca | tccctactg | gctgttgctc | 1500 |
| acgccccagc | acctcaacgt | catcaaggcc | gacttcaacc | ccatgcccaa | ccgtggcacc | 1560 |
| cacaactgtc | gcaaccgcaa | cagcttcaag | ctcagccgtg | tgccgctctc | caccgtgctg | 1620 |
| ctggacccca | cacgcagctg | tacccagcct | cggggcgcct | ttgctgatgg | ccacgtgc | 1678 |

<210> SEQ ID NO 3
<211> LENGTH: 3318
<212> TYPE: DNA
<213> ORGANISM: Homo sapiens

<400> SEQUENCE: 3

| | | | | | |
|---|---|---|---|---|---|
| aattccagtt | taatactaac | cctaatgtgt | gactgcggtt | tacaaagagc | tctgtatcac | 60 |
| ctgggatagc | tttcagtagc | aattcactac | aactggtcct | aaaaaataat | aacaataata | 120 |
| ataataatta | gagaattaaa | acccaacagc | atgttgaatg | gttaaaatca | cgtaagaact | 180 |
| gaaatttggg | gtgggggtgt | cctcaacagc | tgagcttgtc | ctagcagtga | aaatgctcgc | 240 |

-continued

| | | | |
|---|---|---|---|
| ctccaagcag | ggctcagaaa | ggtctggagc cctccaggca gagggctgag ctcaggggc | 300 |
| tcttggagga | cactcacccc | atggtccatg ggatgcttct ggcttcctta aaaacagttg | 360 |
| ggcatccgca | ttgtataagt | aggtggagac cctagtgtgg ttcttttgaa ggatatggga | 420 |
| agggaggatg | acgaactaga | gaagtgggag gggaccaaaa tcactgaggt cccagaatat | 480 |
| catagatttg | ggtataggat | tggggtcact aagaattgag caccaggaat tccagcttct | 540 |
| tcccattaaa | gaaactggga | ctggttttgc cttggaggcc tatgtagtgt tttctgcccc | 600 |
| tgtcccatac | caagtctcat | tgatatttct gcagaatatc agatgaaaat ctatttctaa | 660 |
| agaccattgg | gagaatgggt | ggtggagaag gagttggagt gggggttgggg ggcagttaaa | 720 |
| aatgaataaa | aatctctcag | ctacagaacc caaacatcac ttccctccgc attcacagca | 780 |
| tttcccagca | gtccccagat | ggttgtttcc gtggggacac agcagctgcc tcatttccct | 840 |
| tcaggcccca | tgggctgctg | gtcaacctca ggatctacta agatgacgc aaatgccgac | 900 |
| tgaacaatct | gaaacccaaa | ggactcgagg agagacatgt tctgctgagg agagaaaggt | 960 |
| gagccaaggg | cagggcccag | gtcccccagg gggcccccga gagcccggac atgcaccttc | 1020 |
| tggatgtgtt | tgttcaagta | ggacttagag cggaagaagc tcccacattc agggcatggg | 1080 |
| tacttcttct | ccccatcaga | ctccattttg tttttgggga ctgccatgtc gcaggagaaa | 1140 |
| gagccattgg | cactctgctt | ctctggcgtc ttcaggtcgc tggcatctga gaggtcacca | 1200 |
| taggagtcag | agctctcaat | cggatcctga tgtgagcatt tctggccttc tcggttacag | 1260 |
| atactgcaga | agttgctggg | cccctcgctg tgcttcttca ggtggtctgc catgtatgct | 1320 |
| gcccgcaagt | acttcccaca | cacctggcag ggcaccttgt cttcatgaca ggccaggtgg | 1380 |
| gagcgcagac | ggtctcgggt | ggcaaaagaa gcattgcagg tctgacactt gtgaggccgc | 1440 |
| tcagaagtgt | gcacctgctt | gatatgtccg ttcaagtgat caggcctgga gaagcctttc | 1500 |
| ccacagctct | ggcagatgta | aggcggaatt cccagagaa gaagggtggt gaagactccc | 1560 |
| ggctctcagc | tgcccctgc | atcagaccca gcagctcccc tcccactgtg ctcccgcat | 1620 |
| ctgcctccct | gccccagccc | atcctctcta accaaggaat catgttcgtt caggaggagg | 1680 |
| ccctggccag | cagcctctcg | tccactgaca gtctgactcc cgagcaccag cccattgccc | 1740 |
| agggatgttc | tgattccttg | gagtccatcc ctgcgggaca ggcagcttcc gatgatttaa | 1800 |
| gggacgtgcc | aggagctgtt | ggtggtgcaa gcccagaaca tgccgagccg gaggtccagg | 1860 |
| tggtgccggg | gtctggccag | atcatcttcc tgcccttcac ctgcattggc tacacggcca | 1920 |
| ccaatcagga | cttcatccag | cgcctgagca cactgatccg gcaggccatc gagcggcagc | 1980 |
| tgcctgcctg | gatcgaggct | gccaaccagc gggaggaggg ccaggtgaa cagggcgagg | 2040 |
| aggaggatga | ggaggaggaa | gaagaggagg acgtggctga gaaccgctac tttgaaatgg | 2100 |
| ggccccccaga | cgtggaggag | gaggagggag gaggccaggg ggaggaagag gaggaggaag | 2160 |
| aggaggatga | agaggccgag | gaggagcgcc tggctctgga atgggccctg ggcgcggacg | 2220 |
| aggacttcct | gctggagcac | atccgcatcc tcaaggtgct gtggtgcttc ctgatccatg | 2280 |
| tgcagggcag | tatccgccag | ttcgccgcct gccttgtgct caccgacttc ggcatcgcag | 2340 |
| tcttcgagat | cccgcaccag | gagtctcggg gcagcagcca gcacatcctc tcctccctgc | 2400 |
| gctttgtctt | ttgcttcccg | catggcgacc tcaccgagtt tggcttcctc atgccggagc | 2460 |
| tgtgtctggt | gctcaaggta | cggcacagtg agaacacgct cttcattatc tcggacgccg | 2520 |
| ccaacctgca | cgagttccac | gcggacctgc gctcatgctt gcaccccag cacatggcca | 2580 |
| tgctgtgtag | ccccatcctc | tacggcagcc acaccagcct gcaggagttc ctgcgccagc | 2640 |

-continued

| | | | | |
|---|---|---|---|---|
| tgctcacctt | ctacaaggtg | gctggcggct | gccaggagcg | cagccagggc | tgcttccccg | 2700 |
| tctacctggt | ctacagtgac | aagcgcatgg | tgcagacggc | cgccgggac | tactcaggca | 2760 |
| acatcgagtg | ggccagctgc | acactctgtt | cagccgtgcg | gcgctcctgc | tgcgcgccct | 2820 |
| ctgaggccgt | caagtccgcc | gccatcccct | actggctgtt | gctcacgccc | cagcacctca | 2880 |
| acgtcatcaa | ggccgacttc | aaccccatgc | caaccgtgg | cacccacaac | tgtcgcaacc | 2940 |
| gcaacagctt | caagctcagc | cgtgtgccgc | tctccaccgt | gctgctggac | cccacacgca | 3000 |
| gctgtaccca | gcctcggggc | gcctttgctg | atggccacgt | gctagagctg | ctcgtggggt | 3060 |
| accgctttgt | cactgccatc | ttcgtgctgc | cccacgagaa | gttccacttc | ctgcgcgtct | 3120 |
| acaaccagct | gcgggcctcg | ctgcaggacc | tgaagactgt | ggtcatcgcc | aagacccccg | 3180 |
| ggacgggagg | cagcccccag | ggctcctttg | cggatggcca | gcctgccgag | cgcagggcca | 3240 |
| gcaatgacca | gcgtcccag | gaggtcccag | cagaggctct | ggccccggcc | ccagtggaag | 3300 |
| tcccagctcc | agccccgg | | | | | 3318 |

<210> SEQ ID NO 4
<211> LENGTH: 895
<212> TYPE: DNA
<213> ORGANISM: Homo sapiens

<400> SEQUENCE: 4

| | | | | | | |
|---|---|---|---|---|---|---|
| gaggaggagg | aagaggagga | tgaagaggcc | gaggaggagc | gcctggctct | ggaatgggcc | 60 |
| ctgggcgcgg | acgaggactt | cctgctggag | cacatccgca | tcctcaaggt | gctgtggtgc | 120 |
| ttcctgatcc | atgtgcaggg | cagtatccgc | cagttcgccg | cctgccttgt | gctcaccgac | 180 |
| ttcggcatcg | cagtcttcga | gatcccgcac | caggagtctc | ggggcagcag | ccagcacatc | 240 |
| ctctcctccc | tgcgctttgt | cttttgcttc | ccgcatggcg | acctcaccga | gtttggcttc | 300 |
| ctcatgccga | agctgtgtct | ggtgctcaag | gtacggcaca | gtgagaacac | gctcttcatt | 360 |
| atctcggacg | ccgccaacct | gcacgagttc | cacgcggacc | tgcgctcatg | ctttgcaccc | 420 |
| cagcacatgg | ccatgctgtg | tagccccatc | ctctacggca | gccacaccag | cctgcaggag | 480 |
| ttcctgcgcc | agctgctcac | cttctacaag | gtggctggcg | gctgccagga | gcgcagccag | 540 |
| ggctgcttcc | ccgtctacct | ggtctacagt | gacaagcgca | tggtgcagac | ggccgccggg | 600 |
| gactactcag | gcaacatcga | gtgggccagc | tgcacactct | gttcagccgt | gcggcgctcc | 660 |
| tgctgcgcgc | cctctgaggc | cgtcaagtcc | gccgccatcc | cctactggct | gttgctcacg | 720 |
| ccccagcacc | tcaacgtcat | caaggccgac | ttcaaccca | tgcccaaccg | tggcacccac | 780 |
| aactgtcgca | accgcaacag | cttcaagctc | agccgtgtgc | cgctctccac | cgtgctgctg | 840 |
| gaccccacac | gcagctgtac | ccagcctcgg | ggcgcctttg | ctgatggcca | cgtgc | 895 |

<210> SEQ ID NO 5
<211> LENGTH: 1171
<212> TYPE: DNA
<213> ORGANISM: Homo sapiens

<400> SEQUENCE: 5

| | | | | | | |
|---|---|---|---|---|---|---|
| gaggaggagg | aagaggagga | tgaagaggcc | gaggaggagc | gcctggctct | ggaatgggcc | 60 |
| ctgggcgcgg | acgaggactt | cctgctggag | cacatccgca | tcctcaaggt | gctgtggtgc | 120 |
| ttcctgatcc | atgtgcaggg | cagtatccgc | cagttcgccg | cctgccttgt | gctcaccgac | 180 |
| ttcggcatcg | cagtcttcga | gatcccgcac | caggagtctc | ggggcagcag | ccagcacatc | 240 |
| ctctcctccc | tgcgctttgt | cttttgcttc | ccgcatggcg | acctcaccga | gtttggcttc | 300 |

-continued

```
ctcatgccgg agctgtgtct ggtgctcaag gtacggcaca gtgagaacac gctcttcatt      360
atctcggacg ccgccaacct gcacgagttc cacgcggacc tgcgctcatg ctttgcaccc      420
cagcacatgg ccatgctgtg tagccccatc ctctacggca ccacaccag cctgcaggag       480 ttcctgcgcc agctgctcac cttctacaag gtggctggcg gctgccagga gcgcagccag      540
ggctgcttcc ccgtctacct ggtctacagt gacaagcgca tggtgcagac ggccgccggg      600
gactactcag gcaacatcga gtgggccagc tgcacactct gttcagccgt gcggcgctcc      660
tgctgcgcgc cctctgaggc cgtcaagtcc gccgccatcc cctactggct gttgctcacg      720
ccccagcacc tcaacgtcat caaggccgac ttcaaccca tgcccaaccg tggcacccac       780
aactgtcgca accgcaacag cttcaagctc agccgtgtgc cgctctccac cgtgctgctg      840
gaccccacac gcagctgtac ccagcctcgg ggcgcctttg ctgatggcca cgtgctagag      900
ctgctcgtgg ggtaccgctt tgtcactgcc atcttcgtgc tgccccacga gaagttccac      960
ttcctgcgcg tctacaacca gctgcgggcc tcgctgcagg acctgaagac tgtggtcatc     1020
gccaagaccc ccgggacggg aggcagcccc cagggctcct tgcggatgg ccagcctgcc      1080 gagcgcaggg ccagcaatga ccagcgtccc caggaggtcc cagcagaggc tctggccccg     1140
gccccagtgg aagtcccagc tccagccccg g                                     1171
```

<210> SEQ ID NO 6
<211> LENGTH: 651
<212> TYPE: PRT
<213> ORGANISM: Homo sapiens

<400> SEQUENCE: 6

```
Met Thr Gly Gln Val Gly Ala Gln Thr Val Ser Gly Gly Lys Arg Ser
 1               5                  10                  15

Ile Ala Gly Leu Thr Leu Val Arg Pro Leu Arg Ser Val His Leu Leu
            20                  25                  30

Asp Met Ser Val Gln Val Ile Arg Pro Gly Glu Ala Phe Pro Thr Ala
        35                  40                  45

Leu Ala Asp Val Arg Arg Asn Ser Pro Glu Lys Lys Gly Gly Glu Asp
    50                  55                  60

Ser Arg Leu Ser Ala Ala Pro Cys Ile Arg Pro Ser Ser Ser Pro Pro
65                  70                  75                  80

Thr Val Ala Pro Ala Ser Ala Ser Leu Pro Gln Pro Ile Leu Ser Asn
                85                  90                  95

Gln Gly Ile Met Phe Val Gln Glu Glu Ala Leu Ala Ser Ser Leu Ser
            100                 105                 110

Ser Thr Asp Ser Leu Thr Pro Glu His Gln Pro Ile Ala Gln Gly Cys
        115                 120                 125

Ser Asp Ser Leu Glu Ser Ile Pro Ala Gly Gln Ala Ala Ser Asp Asp
    130                 135                 140

Leu Arg Asp Val Pro Gly Ala Val Gly Gly Ala Ser Pro Glu His Ala
145                 150                 155                 160

Glu Pro Glu Val Gln Val Val Pro Gly Ser Gly Gln Ile Ile Phe Leu
                165                 170                 175

Pro Phe Thr Cys Ile Gly Tyr Thr Ala Thr Asn Gln Asp Phe Ile Gln
            180                 185                 190

Arg Leu Ser Thr Leu Ile Arg Gln Ala Ile Glu Arg Gln Leu Pro Ala
        195                 200                 205

Trp Ile Glu Ala Ala Asn Gln Arg Glu Glu Gly Gln Gly Glu Gln Gly
    210                 215                 220
```

-continued

```
Glu Glu Glu Asp Glu Glu Glu Glu Glu Asp Val Ala Glu Asn
225                 230                 235             240

Arg Tyr Phe Glu Met Gly Pro Pro Asp Val Glu Glu Glu Gly Gly
                245                 250                 255

Gly Gln Gly Glu Glu Glu Glu Glu Glu Asp Glu Glu Ala Glu
            260                 265                 270

Glu Glu Arg Leu Ala Leu Glu Trp Ala Leu Gly Ala Asp Glu Asp Phe
        275                 280                 285

Leu Leu Glu His Ile Arg Ile Leu Lys Val Leu Trp Cys Phe Leu Ile
    290                 295                 300

His Val Gln Gly Ser Ile Arg Gln Phe Ala Ala Cys Leu Val Leu Thr
305                 310                 315                 320

Asp Phe Gly Ile Ala Val Phe Glu Ile Pro His Gln Glu Ser Arg Gly
                325                 330                 335

Ser Ser Gln His Ile Leu Ser Ser Leu Arg Phe Val Phe Cys Phe Pro
            340                 345                 350

His Gly Asp Leu Thr Glu Phe Gly Phe Leu Met Pro Glu Leu Cys Leu
        355                 360                 365

Val Leu Lys Val Arg His Ser Glu Asn Thr Leu Phe Ile Ile Ser Asp
    370                 375                 380

Ala Ala Asn Leu His Glu Phe His Ala Asp Leu Arg Ser Cys Phe Ala
385                 390                 395                 400

Pro Gln His Met Ala Met Leu Cys Ser Pro Ile Leu Tyr Gly Ser His
                405                 410                 415

Thr Ser Leu Gln Glu Phe Leu Arg Gln Leu Leu Thr Phe Tyr Lys Val
            420                 425                 430

Ala Gly Gly Cys Gln Glu Arg Ser Gln Gly Cys Phe Pro Val Tyr Leu
        435                 440                 445

Val Tyr Ser Asp Lys Arg Met Val Gln Thr Ala Gly Asp Tyr Ser
    450                 455                 460

Gly Asn Ile Glu Trp Ala Ser Cys Thr Leu Cys Ser Ala Val Arg Arg
465                 470                 475                 480

Ser Cys Cys Ala Pro Ser Glu Ala Val Lys Ser Ala Ala Ile Pro Tyr
                485                 490                 495

Trp Leu Leu Thr Pro Gln His Leu Asn Val Ile Lys Ala Asp Phe
            500                 505                 510

Asn Pro Met Pro Asn Arg Gly Thr His Asn Cys Arg Asn Arg Asn Ser
        515                 520                 525

Phe Lys Leu Ser Arg Val Pro Leu Ser Thr Val Leu Leu Asp Pro Thr
    530                 535                 540

Arg Ser Cys Thr Gln Pro Arg Gly Ala Phe Ala Asp Gly His Val Leu
545                 550                 555                 560

Glu Leu Leu Val Gly Tyr Arg Phe Val Thr Ala Ile Phe Val Leu Pro
                565                 570                 575

His Glu Lys Phe His Phe Leu Arg Val Tyr Asn Gln Leu Arg Ala Ser
            580                 585                 590

Leu Gln Asp Leu Lys Thr Val Val Ile Ala Lys Thr Pro Gly Thr Gly
        595                 600                 605

Gly Ser Pro Gln Gly Ser Phe Ala Asp Gly Gln Pro Ala Glu Arg Arg
    610                 615                 620
```

-continued

Ala Ser Asn Asp Gln Arg Pro Gln Glu Val Pro Ala Glu Ala Leu Ala
625                 630                 635                 640

Pro Ala Pro Val Glu Val Pro Ala Pro Ala Pro
                645                 650

<210> SEQ ID NO 7
<211> LENGTH: 390
<212> TYPE: PRT
<213> ORGANISM: Homo sapiens

<400> SEQUENCE: 7

Glu Glu Glu Glu Glu Asp Glu Glu Ala Glu Glu Arg Leu Ala
 1               5                  10                 15

Leu Glu Trp Ala Leu Gly Ala Asp Glu Asp Phe Leu Leu Glu His Ile
                20                  25                  30

Arg Ile Leu Lys Val Leu Trp Cys Phe Leu Ile His Val Gln Gly Ser
                35                  40                  45

Ile Arg Gln Phe Ala Ala Cys Leu Val Leu Thr Asp Phe Gly Ile Ala
        50                  55                  60

Val Phe Glu Ile Pro His Gln Gly Ser Arg Gly Ser Ser Gln His Ile
65                  70                  75                  80

Leu Ser Ser Leu Arg Phe Val Phe Cys Phe Pro His Gly Asp Leu Thr
                85                  90                  95

Glu Phe Gly Phe Leu Met Pro Glu Leu Cys Leu Val Leu Lys Val Arg
            100                 105                 110

His Ser Glu Asn Thr Leu Phe Ile Ile Ser Asp Ala Ala Asn Leu His
        115                 120                 125

Glu Phe His Ala Asp Leu Arg Ser Cys Phe Ala Pro Gln His Met Ala
130                 135                 140

Met Leu Cys Ser Pro Ile Leu Tyr Gly Ser His Thr Ser Leu Gln Glu
145                 150                 155                 160

Phe Leu Arg Gln Leu Leu Thr Phe Tyr Lys Val Ala Gly Gly Cys Gln
                165                 170                 175

Glu Arg Ser Gln Gly Cys Phe Pro Val Tyr Leu Val Tyr Ser Asp Lys
            180                 185                 190

Arg Met Val Gln Thr Ala Ala Gly Asp Tyr Ser Gly Asn Ile Glu Trp
        195                 200                 205

Ala Ser Cys Thr Leu Cys Ser Ala Val Arg Arg Ser Cys Cys Ala Pro
210                 215                 220

Ser Glu Ala Val Lys Ser Ala Ala Ile Pro Tyr Trp Leu Leu Leu Thr
225                 230                 235                 240

Pro Gln His Leu Asn Val Ile Lys Ala Asp Phe Asn Pro Met Pro Asn
                245                 250                 255

Arg Gly Thr His Asn Cys Arg Asn Arg Asn Ser Phe Lys Leu Ser Arg
            260                 265                 270

Val Pro Leu Ser Thr Val Leu Leu Asp Pro Thr Arg Ser Cys Thr Gln
        275                 280                 285

Pro Arg Gly Ala Phe Ala Asp Gly His Val Leu Glu Leu Leu Val Gly
290                 295                 300

Tyr Arg Phe Val Thr Ala Ile Phe Val Leu Pro His Glu Lys Phe His
305                 310                 315                 320

Phe Leu Arg Val Tyr Asn Gln Leu Arg Ala Ser Leu Gln Asp Leu Lys
                325                 330                 335

Thr Val Val Ile Ala Lys Thr Pro Gly Thr Gly Gly Ser Pro Gln Gly
            340                 345                 350

```
Ser Phe Ala Asp Gly Gln Pro Ala Glu Arg Arg Ala Ser Asn Asp Gln
        355                 360                 365

Arg Pro Gln Glu Val Pro Ala Glu Ala Leu Ala Pro Ala Pro Val Glu
    370                 375                 380

Val Pro Ala Pro Ala Pro
385                 390

<210> SEQ ID NO 8
<211> LENGTH: 20
<212> TYPE: DNA
<213> ORGANISM: Homo sapiens

<400> SEQUENCE: 8
cttgaggatg cggatgtgct                                                   20

<210> SEQ ID NO 9
<211> LENGTH: 18
<212> TYPE: DNA
<213> ORGANISM: Homo sapiens

<400> SEQUENCE: 9 ccatgggtg agtgtcct                                                      18

<210> SEQ ID NO 10
<211> LENGTH: 18
<212> TYPE: DNA
<213> ORGANISM: Homo sapiens

<400> SEQUENCE: 10
aggacactca ccccatgg                                                     18

<210> SEQ ID NO 11
<211> LENGTH: 20
<212> TYPE: DNA
<213> ORGANISM: Homo sapiens

<400> SEQUENCE: 11
gtatgggaca ggggcagaaa                                                   20

<210> SEQ ID NO 12
<211> LENGTH: 20
<212> TYPE: DNA
<213> ORGANISM: Homo sapiens

<400> SEQUENCE: 12
tttctaaaga ccattgggag                                                   20

<210> SEQ ID NO 13
<211> LENGTH: 20
<212> TYPE: DNA
<213> ORGANISM: Homo sapiens

<400> SEQUENCE: 13
ccattttaaa gtagcggttc                                                   20

<210> SEQ ID NO 14
<211> LENGTH: 20
<212> TYPE: DNA
<213> ORGANISM: Homo sapiens
```

```
<210> SEQ ID NO 14
<211> LENGTH: 20
<212> TYPE: DNA
<213> ORGANISM: Homo sapiens

<400> SEQUENCE: 14
aggagagaaa ggtgagccaa                                               20

<210> SEQ ID NO 15
<211> LENGTH: 20
<212> TYPE: DNA
<213> ORGANISM: Homo sapiens

<400> SEQUENCE: 15
gtagatcctg aggttgacca                                               20

<210> SEQ ID NO 16
<211> LENGTH: 20
<212> TYPE: DNA
<213> ORGANISM: Homo sapiens

<400> SEQUENCE: 16
tgtgagcatt tctggccttc                                               20

<210> SEQ ID NO 17
<211> LENGTH: 20
<212> TYPE: DNA
<213> ORGANISM: Homo sapiens

<400> SEQUENCE: 17
tgaagacgcc agagaagcag                                               20

<210> SEQ ID NO 18
<211> LENGTH: 20
<212> TYPE: DNA
<213> ORGANISM: Homo sapiens

<400> SEQUENCE: 18
gcctcacaag tgtcagacct                                               20

<210> SEQ ID NO 19
<211> LENGTH: 18
<212> TYPE: DNA
<213> ORGANISM: Homo sapiens

<400> SEQUENCE: 19
agaagggtgg tgaagact                                                 18

<210> SEQ ID NO 20
<211> LENGTH: 20
<212> TYPE: DNA
<213> ORGANISM: Homo sapiens

<400> SEQUENCE: 20
cttggttaga gaggatgggc                                               20

<210> SEQ ID NO 21
<211> LENGTH: 20
<212> TYPE: DNA
<213> ORGANISM: Homo sapiens

<400> SEQUENCE: 21
gcccatcctc tctaaccaag                                               20
```

DNA SEQUENCE ENCODING A HUMAN IMIDAZOLINE RECEPTOR AND METHOD FOR CLONING THE SAME

REFERENCE TO RELATED APPLICATION

This application is a division of application Ser. No. 08/650,766, filed May 20, 1996, U.S. Pat. No. 6,015,690 which is a continuing application of Ser. No. 60/012,600, filed Mar. 1, 1996, abandoned.

BACKGROUND OF THE INVENTION

1. Field of the Invention

The present invention is directed to a cDNA clone encoding a human imidazoline receptive protein, designated as an imidazoline receptor subtype-1 (abbreviated $IR_1$), and fragments thereof. Also, the invention relates to an $IR_1$ polypeptide encoded by the cDNA, as well as fragments containing the receptor binding site(s). The invention also relates to methods for producing such a cDNA clone, methods for expressing the $IR_1$ protein, and uses thereof.

2. Description of Related Art

It is believed that brainstem imidazoline receptors possess binding site(s) for therapeutically relevant imidazoline compounds, such as clonidine and idazoxan. These drugs represent the first generation of ligands for the binding site(s) of imidazoline receptors. However, clonidine and idazoxan are also known to possess high affinity for $\alpha_2$-adrenergic receptors. Second generation ligands, such as moxonidine, possess somewhat improved selectivity for $IR_1$ over $\alpha_2$-adrenergic receptors, but more selective compounds for $IR_1$ are needed.

An imidazoline receptor clone is of particular interest because of its potential utility in identifying novel pharmaceutical agents having greater potency and/or more selectivity than currently available ligands have for imidazoline receptors. Recent technological advances permit pharmaceutical companies to use combinatorial chemistry techniques to rapidly screen a cloned receptor for ligands (drugs) binding thereto. Thus, a cloned imidazoline receptor would be of significant value to a drug discovery program.

Until now, the molecular nature of imidazoline receptors remains unknown. For instance, no amino acid sequence data for $IR_1$, e.g., by N-terminal sequencing, has been reported. Three different techniques have been described in the literature by three different laboratories to visualize imidazoline-selective binding proteins (imidazoline receptor candidates) using gel electrophoresis. Some important consistencies have emerged from these results despite the diversity of the techniques employed. On the other hand, multiple protein bands have been identified, which suggests heterogeneity amongst imidazoline receptors. These reports are discussed below. Some of the abbreviations used hereinbelow, have the following meanings:

| | |
|---|---|
| $\alpha_2$AR | Alpha-2 adrenoceptor |
| BAC | Bovine adrenal chromaffin |
| ECL | Enhanced chemiluminescence (protein detection procedure) |
| EST | Expressed Sequence Tag |
| I-site | Any imidazoline-receptive binding site (e.g., encoded on $IR_1$) |
| $IR_1$ | Imidazoline receptor subtype$_1$ |
| IR-Ab | Imidazoline receptor antibody |
| $I_2$Site | Imidazoline binding subtype$_2$ |
| kDa | Kilodaltons (molecular size) |
| MAO | monoamine oxidase |
| MW | molecular weight |
| NRL | European abbreviation for RVLM (see below) |
| PC-12 | Phaeochromocytoma-12 cells |
| $^{125}$PIC | [$^{125}$I]p-iodoclonidine |
| PKC | Protein Kinase C |
| RVLM | Rostral Ventrolateral Medulla in brainstem |
| SDS | sodium dodecyl sulfate gel electrophoresis |

Reis et al. [Wang et al., *Mol. Pharm.*, 42: 792–801 (1992); Wang et al., *Mol. Pharm.*, 43: 509–515 (1993)] were the first to demonstrate partial purification of an imidazoline-selective binding protein and to characterize it as having MW=70 kDa. This was accomplished using bovine cells (BAC), which lack an $\alpha_2$AR [Powis & Baker, *Mol. Pharm.*, 29:134–141 (1986)]. The 70 kDa imidazoline-selective protein in those studies had high affinities for both idazoxan and p-aminoclonidine affinity chromatography columns. To date, no one has reported the complete purification of this imidazoline receptor protein. Likewise, no amino acid sequences have been reported for $IR_1$.

The partially purified 70 kDa protein was used by Reis and co-workers to raise "I-site binding antiserum", designated herein as Reis antiserum. The term "I-site" refers to the imidazoline binding site, presumably defined within the imidazoline receptor protein. Reis antiserum was prepared by injecting the purified protein into rabbits [Wang et al, 1992]. The first immunization was done subcutaneously with the protein antigen (10 µg) emulsified in an equal volume of complete Freund's adjuvant, and the next three booster shots were given at 15-day intervals with incomplete Freund's adjuvant. The polyclonal antiserum has been mostly characterized by immunoblotting, but radioimmunoassays (RIA) and/or conjugated assay procedures, i.e., ELISA assays, are also conceivable [see "Radioimmunoassay of Gut Regulatory Peptides: Methods in Laboratory Medicine," Vol. 2, chapters 1 and 2, Praeger Scientific Press, 1982].

The present inventors and others [Escriba et al., *Neurosci. Lett.* 178: 81–84 (1994)] have characterized the Reis antiserum in several respects. For instance, the present inventors have discovered that human platelet immunoreactivity with Reis antiserum is mainly confined to a single protein band of MW=33 kDa, although a trace band at 85 kDa was also observed. This 33 kDa band was enriched in plasma membrane fractions as expected for an imidazoline receptor. Furthermore, the intensity of this band was found to be positively correlated with non-adrenergic $^{125}$PIC Bmax values at platelet $IR_1$ sites in samples from the same subjects, with an almost one-to-one slope factor. In addition, the nonadrenergic $^{125}$PIC binding sites on platelets were discovered by the present inventors to have the same rank order of affinities as $IR_1$ binding sites in brainstem [Piletz and Sletten, *J.Pharm. & Exper. Therap.*, 267: 1493–1502 (1993)]. The platelet 33 kDa band may also be a product of a larger protein, since in human megakaryoblastoma cells, which are capable of forming platelets in tissue cultures, an 85 kDa immunoreactive band was found to predominate.

Immunoreactivity with Reis antiserum does not appear to be directed against human $\alpha_2$AR and/or MAO A/B. This is significant because $\alpha_2$AR and MAO A/B have previously been cloned and also bind to imidazolines. The present inventors have obtained selective antibodies and recombinant preparations for $\alpha_2$AR and MAO A/B, and these proteins do not correspond to the 33, 70, or 85 kDa putative IR$_1$ bands. Thus, there is substantial evidence that, at least in human platelets, the Reis antiserum is IR$_1$ selective.

Another antiserum was raised by Drs. Dontenwill and Bousquet in France [Greney et al., *Europ. J. Pharmacol.*, 265: R1–R2 (1994); Greney et al., *Neurochem. Int.*, 25: 183–191 (1994); Bennai et al., *Annals NY Acad. Sci.*, 763: 140–148 (1995)] against polyclonal antibodies for idazoxan (designated Dontenwill antiserum). This anti-idiotypic antiserum inhibits $^3$H-clonidine but not $^3$H-rauwolscine ($\alpha_2$-selective) binding sites in the brainstem, suggesting it interacts with IR$_1$ [Bennai et al., 1995]. As shown in FIG. 1, human RVLM (same as NRL) membrane fractions displayed bands of 41 and 44 kDa, as detected by the present inventors using this anti-idiotypic antiserum.

The present inventors have found that the bands of MW=41 and 44 kDa detected by Dontenwill antiserum may be derived from an 85 kDa precursor protein, similar to that occurring in platelet precursor cells. An 85 kDa immunoreactive protein is obtained in fresh rat brain membranes only when a cocktail of 11 protease inhibitors is used. Also, as shown in FIG. 1, it is found that Reis antiserum detects the 41 and 44 kDa bands in human brain when fewer protease inhibitors are used.

Additionally, the Dontenwill antiserum weakly detects the platelet 33 kDa band. Thus, the present inventors have hypothesized that the 41 and 44 kDa immunoreactive proteins may be alternative breakdown products of an 85 kDa protein, as opposed to the platelet 33 kDa breakdown product.

In summary, the main conclusion from the above results is that, despite vastly different origins, the Reis and Dontenwill antisera both detect identical bands in human platelets, RVLM, and hippocampus.

Using yet another technique, a photoaffinity imidazoline ligand, $^{125}$AZIPI, has also been developed to preferentially label I$_2$-imidazoline binding sites [Lanier et al., *J.Biol.Chem.*, 268: 16047–16051 (1993)]. The $^{125}$AZIPI photoaffinity ligand was used to visualize 55 kDa and 61 kDa binding proteins from rat liver and brain. It is believed that the 61 kDa protein is probably MAO, in agreement with other findings [Tesson et al., *J.Biol.Chem.*, 270: 9856–9861 (1995)] showing that MAO proteins bind certain imidazoline compounds. The different molecular weights between these bands and those studied by the present inventors is one of many pieces of evidence that distinguishes IR$_1$ from I$_2$ sites.

To the inventors' knowledge and as described herein, we are first to clone a cDNA encoding a protein with the immunological and ligand binding properties expected of an IR$_1$. We are first to identify the nucleotide sequence of a DNA molecule encoding an imidazoline receptor, and first to determine the amino acid sequence of an imidazoline receptor. The polypeptides described herein are clearly distinct from $\alpha_2$AR or MAO A/B proteins.

SUMMARY OF THE INVENTION

The present invention is for an isolated polypeptide that is receptive to (binds to) an imidazoline compound. Exemplary imidazoline compounds in this context are p-iodoclonidine and moxonidine. Typically, such a polypeptide immunoreacts with Reis antiserum and/or Dontenwill antiserum.

In one aspect of the invention, a polypeptide includes a 651 amino acid sequence as shown in SEQ ID No. 6. Other imidazoline receptive proteins homologous to this polypeptide are also contemplated. Such a protein generally has a molecular weight of about 60 to 80 kDa. More particularly, it can have a molecular weight of about 70 kDa.

In another aspect of the invention, a polypeptide includes a 390 amino acid sequence as shown in SEQ ID No. 7. Such a polypeptide generally has a molecular weight of about 35 to 45 kDa. More particularly, it can have a molecular weight of about 37 kDa.

A DNA molecule encoding an aforementioned imidazoline-receptive polypeptide is also contemplated. Such a DNA molecule, e.g., a cDNA derived from mRNA, can contain a nucleotide sequence encoding the amino acid sequence shown in SEQ ID No. 6. Thus, a DNA molecule containing the 1678 base pair (b.p.) (1677/3=559) nucleotide sequence shown in SEQ ID No. 2 is contemplated. In another embodiment, a DNA molecule includes the longer nucleotide sequence shown in SEQ ID No. 3.

In another embodiment of the invention, a DNA molecule contains a nucleic acid sequence encoding the amino acid sequence shown in SEQ ID No. 7. Such a DNA molecule can include the 895 base pair nucleic acid sequence shown in SEQ ID No. 4. In another aspect, it can include the 1171 base pair nucleic acid sequence shown in SEQ ID No. 5.

RNA molecules complementary to an instant DNA molecule, e.g., an mRNA molecule (sense) or a complementary cRNA molecule (antisense), is a further aspect of the invention.

A further aspect of the invention is for a recombinant vector, as well as a host cell transfected with the recombinant vector, wherein the recombinant vector contains at least one of the nucleotide sequences shown in SEQ ID Nos. 2–5, or a nucleotide sequence homologous thereto.

A method of producing an imidazoline receptor protein is another aspect of the invention. Such a method entails transfecting a host cell with an aforementioned vector, and culturing the transfected host cell in a culture medium to generate the imidazoline receptor.

A significant further aspect of the invention is a method of screening for a ligand that binds to an imidazoline receptor. Such a method can comprise culturing an above-mentioned host cell in a culture medium to express imidazoline receptor proteins, followed by contacting the proteins with a labelled ligand for the imidazoline receptor under conditions effective to bind the labelled ligand thereto. The imidazoline receptor proteins can then be contacted with a candidate ligand, and any displacement of the labelled ligand from the proteins can be detected. Displacement of labelled ligand signifies that the candidate ligand is a ligand for the imidazoline receptor. These steps can be performed on intact host cells, or on proteins isolated from the cell membranes of the host cells.

The invention will now be described in more detail with reference to specific examples.

DETAILED DESCRIPTION OF THE INVENTION

Figure 1A:
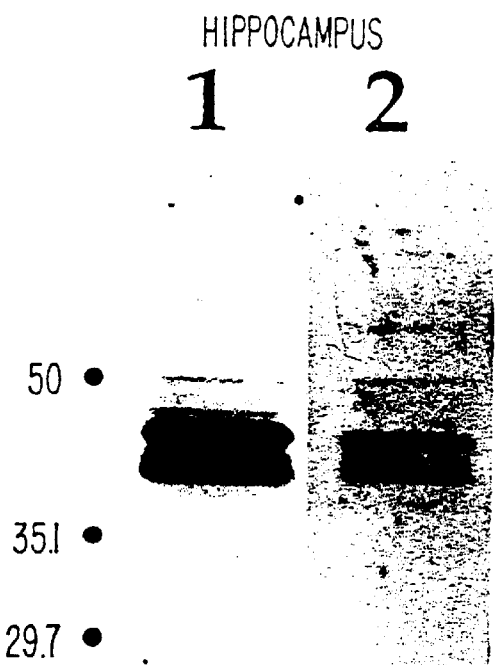
FIG. 1 depicts a comparison of Reis antiserum (lane 1, 1:2000 dilution) and Dontenwill antiserum (lane 2, 1:5000 dilution) immunoreactivities for human NRL (same as RVLM) and hippocampus, as discussed in Example 1.

The present invention concerns multiple aspects of the imidazoline receptor protein, and DNA molecule encoding the same, which have now been discovered.

First, a polypeptide having imidazoline binding activity has been identified, as well as fragments thereof which contain the putative active site for binding, as discussed hereinafter. Although a polypeptide described herein has a binding affinity for an imidazoline compound, it may also have an enzymatic activity, such as do catalytic antibodies and ribozymes.

Exemplary polypeptides are those containing either of the amino acid sequences shown in SEQ ID Nos. 6 or 7 (with the full length (651 residue) amino acid sequence given in SEQ ID No. 6). Functionally equivalent polypeptides are also contemplated, such as those having a high degree of homology with an aforementioned polypeptide, particularly when they contain the Glu-Asp-rich region described hereinafter which is believed to define an active imidazoline binding site.

A polypeptide of the invention can be formed by direct chemical synthesis on a solid support using the carbodiimide method [R. Merrifield, JACS, 85: 2143 (1963)]. Alternatively, and preferably, an instant polypeptide can be produced by a recombinant DNA technique as described herein and elsewhere [e.g., U.S. Pat. No. 4,740,470 (issued to Cohen and Boyer), the disclosure of which is incorporated herein by reference], followed by culturing transformants in a nutrient broth.

Second, a DNA molecule of the present invention encodes an aforementioned polypeptide. Thus, any of the degenerate set of codons encoding an instant polypeptide is contemplated. A particularly preferred coding sequence is the 1678 base pair sequence set forth in SEQ ID No. 2, which has now been discovered to be the native nucleotide sequence that encodes the 70 kDa human $IR_1$ protein of the invention. In another embodiment, a DNA molecule includes the 3318 base pair nucleotide sequence shown in SEQ ID No. 3. This latter sequence includes the nucleotide sequence of SEQ ID No. 2, as well as additional nonplasmid, noncoding cDNA at the 5' and 3' ends of the protein-coding sequence.

In another embodiment of the invention, a DNA molecule contains a nucleic acid sequence encoding the amino acid sequence (390 residues) shown in SEQ ID No. 7. This amino acid sequence corresponds to that derived from direct sequencing of the 5A-1 clone described hereinafter, and represents a C-terminal fragment of the native protein. Preferably, a DNA molecule includes the native 895 base pair nucleic acid sequence shown in SEQ ID No. 4, which was derived from the 5A-1 clone. A DNA molecule can also include the 1171 base pair nucleic acid sequence shown in SEQ ID No. 5, which includes non-plasmid cDNA at its 3' (noncoding) end.

A DNA molecule of the present invention can be synthesized according to the phosphotriester method [Matteucci et al., JACS, 103: 3185 (1988)]. This method is particularly suitable when it is desired to effect site-directed mutagenesis of an instant DNA sequence, whereby a desired nucleotide substitution can be readily made. Another method for making an instant DNA molecule is by simply growing cells transformed with plasmids containing the DNA sequence, lysing the cells, and isolating the plasmid DNA molecules. Preferably, an isolated DNA molecule of the invention is made by employing the polymerase chain reaction (PCR) [e.g., U.S. Pat. No. 4,683,202 (issued to Mullis)] using synthetic primers that anneal to the desired DNA sequence, whereby DNA molecules containing the desired nucleotide sequence are amplified. Also, a combination of the above methods can be employed, such as one in which synthetic DNA is ligated to cDNA to produce a quasi-synthetic gene [e.g., U.S. Pat. No. 4,601,980 (issued to Goeddel et al.))

A further aspect of the invention is for a vector, e.g., a plasmid, that contains at least one of the nucleotide sequences shown in SEQ ID Nos. 2–5. Whenever the reading frame of the vector is appropriately selected, the vector encodes an $IR_1$ polypeptide of the invention. Hence, a fragment of the native $IR_1$ protein is contemplated, as well as fusion proteins that incorporate an amino acid sequence as described herein. Also, a vector containing a nucleotide sequence having a high degree of homology with any of SEQ ID Nos. 2–5 is contemplated within the invention, particularly when it encodes a protein having imidazoline binding activity.

A recombinant vector of the invention can be formed by ligating an afore-mentioned DNA molecule to a preselected expression plasmid, e.g., with T4 DNA ligase. Preferably, the plasmid and DNA molecule are provided with cohesive (overlapping) terminii, with the plasmid and DNA molecule operatively linked (i.e., in the correct reading frame).

Another aspect of the invention is a host cell transfected with a vector of the invention. Relatedly, a protein expressed by a host cell transfected with such a vector is contemplated, which protein may be bound to the cell membrane. Such a protein can be identical with an aforementioned polypeptide, or it can be a fragment thereof, such as when the polypeptide has been partially digested by a protease in the cell. Also, the expressed protein can differ from an aforementioned polypeptide, as whenever it has been subjected to one or more post-translational modifications. For the protein to be useful within the context of the present invention, it still should retain imidazoline binding activity.

A method of producing an imidazoline receptor protein is another aspect of the invention, which entails transfecting a host cell with an aforementioned vector, and culturing the transfected host cell in a culture medium to generate the imidazoline receptor. The receptor molecule can undergo any post-translational modification, including proteolytic decomposition, whereby its structure is altered from the basic amino acid residue sequence encoded by the vector. A suitable transfection method is electroporation, and the like.

With respect to transfecting a host cell with a vector of the invention, it is contemplated that a vector encoding an instant polypeptide can be transfected directly in animals. For instance, embryonic stem cells can be transfected, and the cells can be manipulated in embryos to produce transgenic animals. Methods for performing such an operation have been previously described (Bond et al., Nature, 374:272–276 (1995)]. These methods for expressing an instant cDNA molecule in either tissue culture cells or in animals can be especially useful for drug discovery.

Possibly the most significant aspect of the present invention is in its potential for affording a method of screening for a ligand (drug) that binds to an imidazoline receptor. Such a method comprises culturing an above-mentioned host cell in a culture medium to express an instant imidazoline receptive polypeptide, then contacting the polypeptides with a labelled ligand, e.g., radiolabelled p-iodoclonidine, for the imidazoline receptor under conditions effective to bind the labelled ligand thereto. The polypeptides are further contacted with a candidate ligand, and any displacement of the labelled ligand from the polypeptides is detected. Displacement signifies that the candidate ligand actually binds to the imidazoline receptor. These steps can be performed on intact host cells, or on proteins isolated from the cell membranes of the host cells.

Typically, a suitable drug screening protocol involves preparing cells (or possibly tissues from transgenic animals) that express an instant imidazoline receptive polypeptide. This process is currently referred to as combinatorial chemistry. In this process, categories of chemical structure are systematically screened for binding affinity or activation of the receptor molecule encoded by the transfected cDNA. With respect to the imidazoline receptor, a number of commercially available radioligands, e.g., $^{125}$PIC, can be used for competitive drug binding affinity screening.

An alternative approach is to screen for drugs that elicit or block a second messenger effect known to be coupled to activation of the imidazoline receptor, e.g., moxonidine-stimulated arachidonic acid release. Even with a weak binding affinity or activation by one category of chemicals, systematic variations of that chemical structure can be studied and a preferred compound (drug) can be deduced as being a good pharmaceutical candidate. Identification of this compound would lead to animal testing and upwards to human trials, however, the initial rationale for drug discovery is vastly improved with an instant cloned imidazoline receptor.

Along these lines, a drug screening method is contemplated in which a host cell of the invention is cultured in a culture medium to express an instant imidazoline receptive polypeptide. Intact cells are then exposed to an identified agent (agonist, inverse agonist, or antagonist) under conditions effective to elicit a second messenger or other detectable response upon interacting with the receptor molecule. The imidazoline receptive polypeptides are then contacted with one or more candidate chemical compounds (drugs), and any modification in a second messenger response is detected. Compounds that mimic an identified agonist would be agonist candidates, and those producing the opposite response would be inverse agonist candidates. Those compounds that block the effects of a known agonist would be antagonist candidates for an in vivo imidazoline receptor. For meaningful results, the contacting step with a candidate compound is preferably conducted at a plurality of candidate compound concentrations.

A method of probing for a gene encoding an imidazoline receptor or homologous protein is further contemplated. Such a method comprises providing a DNA molecule identical or complementary to an above-described cDNA molecule, contacting the DNA molecule with genetic material suspected of containing a gene encoding an imidazoline receptor, or homologous protein, under stringent hybridization conditions (e.g., a high stringency wash condition is 0.1×SSC, 0.5% SDS at 65° C.), and identifying any portion of the genetic material that hybridizes to the DNA molecule.

Still further, a method of selectively producing antibodies, e.g., monoclonal antibodies, immunoreactive with an instant imidazoline-receptive protein comprises injecting a mammal with an aforementioned polypeptide, and isolating the antibodies produced by the mammal. This aspect is discussed in more detail in an example presented hereinafter.

The present inventors began their search for a human imidazoline receptor cDNA by screening a λgt11 phage human hippocampus cDNA expression library. Their preliminary research had indicated that both of the known antisera (Reis and Dontenwill) that are directed against human imidazoline receptors were immunoreactive with identical bands in the human hippocampus. By contrast, other brain regions either were commercially unavailable as cDNA expression libraries or yielded inconsistencies between the two antisera. Therefore, it was felt that a human hippocampal cDNA library held the best opportunity for obtaining a cDNA for an imidazoline receptor. Immunoexpression screening was chosen over other cloning strategies because of its sensitivity when coupled with the ECL detection system used by the present inventors, as discussed hereinbelow.

Once an initial clone (5A-1) was identified, a more full-length clone was obtainable after DNA sequence analysis. The binding affinities of the expressed protein after transfection in COS cells were determined by radioligand binding procedures developed in the inventors' laboratory [Piletz and Sletten, 1993, ibid]. A number of unique discoveries, i.e., brain immunoreactivity regionalization studies, and adapting ECL to these antisera, led to our identification of an imidazoline receptor cDNA described herein.

To identify an instant cDNA clone encoding an imidazoline receptor it was necessary to employ both of the known antibodies to imidazoline receptors. These antibodies were obtained by contacting Dr. D. Reis (Cornell University Medical Center, New York City), and Drs. M. Dontenwill and P. Bousquet (Laboratoire de Pharmacologie Cardiovasculaire et Renale, CNRS, Strasbourg, France). These antisera were obtained free of charge and without confidentiality or restrictions on their use. The former antiserum (Reis antiserum): was derived from a published imidazoline receptor protein [Wang et al., (1992, 1993), the disclosures of which are incorporated herein by reference]. The method for raising the latter antiserum (Dontenwill antiserum) has also been published [Bennai et al., (1995), the disclosure of which is incorporated herein by reference]. The latter antiserum was derived using an anti-idiotypic approach that identified the pharmacologically correct (clonidine and idazoxan selective) binding site structure.

EXAMPLE 1

Selectivity of the Antisera

The obtained Reis antiserum had been prepared against a purified imidazoline binding protein isolated from BAC cells, which protein runs in denaturing-SDS gels at 70 kDa [Wang et al., 1992, 1993]. The Dontenwill antiserum is anti-idiotypic, and thus is believed to detect the molecular configuration of an imidazoline binding site domain in any species.

Both of these antisera have been tested to ensure that they are in fact selective for a human imidazoline receptor. In particular, we found that both of these antisera detected identical bands in human platelets and hippocampus, and in brainstem RVlM (NRL) by Western blotting (see FIG. 1). In these studies, in order to increase sensitivity over previously published detection methods, an ECL (Enhanced Chemiluminescence) system was employed. The linearity of response of the ECL system was demonstrated with a standard curve. ECL detection was demonstrated to be very quantifiable and about ten times more sensitive than other methods previously used with these antisera. Western blots with antiserum dilutions of 1:3000 revealed immunoreactivity with as little as 1 ng of protein from a human hippocampal homogenate by dot blot analysis.

Figure 1B:
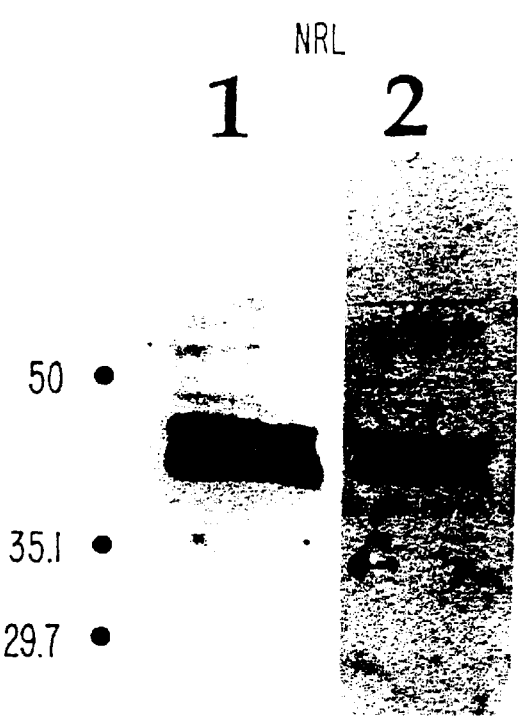

For the studies depicted in FIG. 1, human hippocampal homogenate (30 μg) and NRL membrane proteins (10 μg) were electrophoresed through a 12.5% polyacrylamide gel, electrotransfered to nitrocellulose and sequentially incubated with (1) the Reis antibody (1:2000 dilution) and (2) the Dontenwill antibody (1:5000 dilution). Immunoreactive bands were visualized with an Enhanced Chemiluminescence (ECL) detection kit (Amersham) using anti-rabbit Ig-HRP conjugated antibody at a dilution of 1:3000 and the ECL detection reagents. Following detection with the antibody, blots were stripped and reprocessed omitting the primary antibody to check for complete removal of this antibody. In panels A and B, lane 1 shows the immunoreactive bands observed with the Reis antibody and lane 2 shows the bands detected with the Dontenwill antibody. Protein molecular weight standards are indicated to the left of each panel (in kDa).

Despite the diverse origins of Reis and Dontenwill antisera, both of these antisera detected a 33 kDa band in human platelets. Although this band is of smaller size than that reported for other tissues [Wang et al., 1993; Escriba et al., 1994; Greney et al., 1994], the fact that both antisera detected it suggests an imidazoline binding peptide. The 33 kDa band was enriched in platelet plasma membrane fractions, as is known to be the case for $IR_1$ binding, but not $I_2$ binding [Piletz and Sletten, 1993]. The present investigators also found that human cortex imidazoline receptor—antibody immunoreactivity is enriched in a plasma membrane fraction (pelleted at 100,000×g), but not in a mitochondrial fraction (pelleted at 20,000×g), which suggests that the brain receptor also exists within plasma membranes.

A significant positive correlation was observed within samples from 15 healthy platelet donors between $IR_1$ Bmax values (but not $I_2$ or $\alpha_2AR$ Bmax values), with the $IR_1$ immunoreactivity on Western blots. This correlation exhibited a slope factor close to unity (results not shown). This correlation strongly suggested that an $IR_1$ binding protein could be revealed in an imidazoline receptor—antibody Western blotting assay. Furthermore, the Reis antiserum failed to detect authentic $\alpha_2AR$, MAO A or MAO B bands on gels, i.e., it was not immunoreactive with MAO at MW=61 kDa, or $\alpha_2AR$ at MW=64 kDa. Additionally, no immunoreactive bands were observed using preimmune antiserum. Thus, after extensively characterizing these antisera with human materials, it was concluded that these antisera are indeed selective for a human imidazoline receptor protein.

EXAMPLE 2

Cloning of the Imidazoline Receptor

Figure 2A:
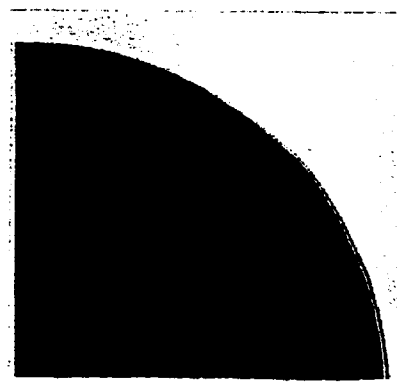
FIG. 2 depicts a comparison of Reis antiserum (1:15,000 dilution) and Dontenwill antiserum (1:20,000 dilution) immunoreactivities for plaques isolated from the human hippocampal cDNA library used in cloning as discussed in Example 2. The plaques contain the initial clone, designated herein as 5A-1, in a third stage of purification.
Figure 2B:
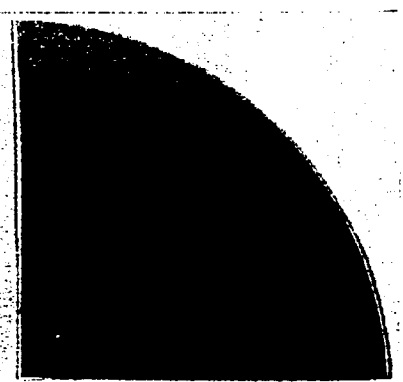

A commercially available human hippocampal cDNA λgt11 expression library (Clontech Inc., Palo Alto, Calif.) was screened for immunoreactivity sequentially using both the anti-idiotypic Dontenwill antiserum and the Reis antiserum. Standard techniques to induce protein and transference to a nitrocellulose overlay were employed. [See, for instance, Sambrook et al., 1989, "Molecular Cloning: A Laboratory Manual," Cold Spring Harbor Laboratory Press]. After washing and blocking with 5% milk, the Dontenwill antiserum was added to the overlay at 1:20,000 dilution in Tris-buffered saline, 0.05% Tween20, and 5% milk. The Reis antiserum was employed similarly, but at 1:15,000 dilution. These high dilutions of primary antiserum were chosen to avoid false positives. Secondary antibody was added, and positive plaques were identified using ECL. Representative results are shown in FIG. 2.

Positive plaques were pulled and rescreened until tertiary screenings yielded only positive plaques. Four separate positive plaques were identified from more than 300,000 primary plaques in our library. Recombinant λgt11 DNA purified from each of the four plaques was subsequently subcloned into *E. coli* pBluescript vector (Stratagene, La Jolla, Calif.). Sequencing of these four cDNA inserts in pBluescript demonstrated that they were identical, suggesting that only one cDNA had actually been identified four times. Thus, the screening had been verified as being highly reproducible and the frequency of occurrence was as expected for a single copy gene, i.e., one in 75,000 transcripts. As shown in FIG. 2, the protein produced by the first positive clone, designated 5A-1, tested positive with both the Reis antiserum and the Dontenwill antiserum. Tertiary-screened plaques of 5A-1 were all immuno-positive with either of the two known anti-imidazoline receptor antisera, but not with either preimmune antisera. These results suggested that clone 5A-1 encoded a fusion peptide similar to or identical with one of the predominant bands detected in human Western blots by both the Dontenwill and Reis antisera.

Sequencing of the four clones was performed by ACGT Company (Chicago, Ill.) after subcloning them into pBluescript vector SK (Stratagene). Both manual and automatic sequencing strategies were employed which are outlined as follows:

Manual Sequencing

1. DNA sequencing was performed using T7 DNA polymerase and the dideoxy nucleotide termination reaction.

2. The primer walking method [Sambrook et al., ibid.] was used in both directions.

3. ($^{35}$S)dATP was used for labelling.

4. The reactions were analyzed on 6% polyacrylamide wedge or non-wedge gels containing 8 M urea, with samples being loaded in the order of A C G T.

5. DNA sequences were analyzed by MacVector Version 5.0. and by various Internet-available programs, i.e., the BLAST program.

Automatic Sequencing

1. DNA sequencing was performed by the fluorescent dye terminator labelling method using AmpliTaq DNA polymerase (Applied Biosystems Inc. Prizm DNA Sequencing Kit, Perkin-Elmer Corp., Foster City, Calif.).

2. The primer walking method was used. The primers actually used were a subset of those shown in SEQ ID Nos. 8–21.

3. Sequencing reactions were analyzed on an Applied Biosystems, Inc. (Foster City, Calif.) sequence analyzer.

These results demonstrated that the initial clone (5A-1) contained a 1171 base pair insert (see SEQ ID No. 5). Only one extended open reading frame for translation into protein was found possible. Consequently, it was determined that the 5A-1 cDNA derived from mRNA encoding 298 amino acids, which ended at a carboxy terminal cysteine (the TAG termination codon was at base pairs 895–898 in the 5A-1 sequence). The 895 base pair nucleotide sequence of the coding region of the 5A-1 clone is shown in SEQ ID No. 4. Thus, clone 5A-1 defined approximately 53% of the 70,000 MW protein predicted.

Using programs and databases available on the Internet (retrieved from NCBI Blast E-mail Server address blast@ncbi.nlm.nih.gov), it was determined that the 5A-1 clone encodes a unique molecule. The BLASTP program-[1.4.8MP, Jun. 20 1995 (build Nov. 13, 1995)] was used to compare all of the possible frames of amino acid sequences encoded by 5A-1 versus all known amino acid sequences available within multiple international databases [Altschul et al., *J. Mol. Biol.*, 215: 403–410 (1990)]. Only one protein, from *Micrococcus luteus*, possessed a marginally significant homology (p=0.04)(41%) over a short stretch of 75 of the 298 amino acids encoded by 5A-1. Otherwise, there were no significant amino acid homologies (i.e., with $p \leq 0.05$) for any known proteins. Therefore, the protein encoded by 5A-1 is not significantly related to MAO A or B, $\alpha_2$AR, or any other known eukaryotic protein in the literature.

In contrast to the amino acid search on BLASTP, two partially homologous cDNA sequences covering 155 and 250 b.p. of the 5A-1 clone were discovered to exist using BLASTN (reached from the same Internet server). BLASTN is a program used to compare known DNA sequences from international databases, regardless of whether they encode a polypeptide. Neither of the two cDNA sequences having high homology to 5A-1 have been reported anywhere else except on the Internet. Both were derived as Expressed Sequence Tags (ESTs) in random attempts to sequence the human cDNA repertoire [as described in Adams et al., *Science*, 252: 1651–1656 (1991)]. As far as can be determined, the discoverers of these ESTs lack any knowledge of the protein they encode. One cDNA, designated HSA09H122, contained 250 b.p. with 7 unknown/incorrect base pairs (97% homology) versus 5A-1 over the same region. HSA09H122 was generated in France (Genethon, B.P. 60, 91002 Evry Cedex France) from a human lymphoblast cDNA library. The other EST, designated EST04033, contained 155 b.p. with 12 unknown/incorrect base pairs (92% homology) versus 5A-1 over the same region. EST04033 was generated at the Institute for Genomic Research (Gaithersburg, Md.) from a human fetal brain cDNA clone (HFBDP28). Thus, both of these ESTs are short DNA sequences and contain a number of errors (typical of single-stranded sequencing procedures as used when randomly screening ESTs).

Based on the BLASTN search, the owner of HSA09H122 was contacted in an effort to obtain that clone. The current owner of the clone appears to be Dr. Charles Auffret (Paul Brousse Hospital, Genetique, B.P. 8, 94801 Villejuif Cedex, France). Dr. Auffret indicated by telephone that his clone came from a lot of clones believed to be contaminated with yeast DNA, and he did not choose to release it. Contamination with yeast DNA was later confirmed to have been reported within an Internet database. Thus, HSA09H122 was not deemed reliable.

The other partial clone (EST04033) was purchase from the American Type Culture Collection (ATCC catalog no. 82815) (Rockville, Md.). A telephone call to the Institute for Genomic Research revealed that it had been deposited at ATCC recently. As far as can be determined, the present inventors were the first to sequence the full length insert of EST04033. The full length of EST04033 sequenced was 3385 base pair (SEQ ID No. 1), with a 3318 base pair nonplasmid insert (see SEQ ID No. 3). Within this sequence of EST04033 the remaining 783 base pairs of the coding sequence predicted for a 70 kDa imidazoline receptor were obtained (i.e., 783 b.p. in EST04033+894 b.p. of 5A-1=1677 total coding nucleotides). The entire 1678 base pair coding region for the 70 kDa protein is shown in SEQ ID No. 2. It is important to note that all of the 155 b.p. reported for EST04033 on the Internet were located at the 3' end outside of the coding region. Thus, the present inventors are first to sequence any of the coding region of an instant imidazoline receptor.

The nucleotide sequence of EST04033 was determined in the same manner as described previously for the 5A-1 clone. The nucleotide sequence of the entire clone is shown in SEQ ID No: 1. In this sequence, an identical overlap was observed for the sequence obtained previously for the 5A-1 clone and the sequence obtained for EST04033. The 5A-1 overlap began at EST04033 b.p. 2,181 and continued to the end of the molecule (b.p. 3,350).

The nucleotide sequence identified contains an open reading frame for a 70 kDa protein, which is the same size as the protein originally isolated as the putative bovine imidazoline receptor purified by Reis and coworkers [Wang et al., 1992] from which the Reis antiserum was subsequently derived [Wang et al., 1993].

Of further interest is a unique glutamic- and aspartic acid-rich coding region within the clone. This region of the $IR_1$ cDNA encodes a highly unique span of 59 amino acids, 36 of which are Glu or Asp residues (61%). This region is largely contained within clone 5A-1 and is just upstream from apparent transmembrane loops and an ultimate polar carboxy terminus tail. Since the Dontenwill antiserum is specifically directed against an idazoxan/clonidine binding site, and its immunoreactivity is directed against the clone 5A-1/λgt11fusion protein, this suggests that clone 5A-1 encodes the binding site of the imidazoline receptor. The identification of this unique Glu/Asp-rich domain within the 5A-1 clone is consistent with an expected negatively charged pocket capable of binding clonidine and agmatine, both of which are highly positively charged ligands. Furthermore, this stretch is located within the longest overall region of homology that the sequence has for any known protein, i.e., the ryanodine receptor (as determined by running EST04033 on BLAST). Specifically, we have discovered four regions of homology between the imidazoline receptor and the ryanodine receptor, which are all Glu/Asp-rich. In this region of the clone the total nucleic acid homology is 67% with the ryanodine receptor DNA sequence. However, this is not sufficient to indicate that the imidazoline receptor is a subtype of the ryanodine receptor, because the homologous sequence is still a minor portion of the 3318 bp sequence identified in the cloned cDNA. Instead, this significant homology may reflect a commonality in function between this region of the $IR_1$ and the ryanodine receptor.

The Glu/Asp-rich region within the ryanodine receptor, which is significantly homologous to clone 5A-1, has been reported to define a calcium and ruthenium red dye binding domain that modulates the ryanodine receptor/Ca++ release channel located within sarcoplasmic reticulum. The only other charged amino acids within the Glu/Asp-rich region are two arginines (the ryanodine receptor has uncharged amino acids at the corresponding positions).

Based on the identification of Arg residues within the Glu/Asp-rich region of the:predicted imidazoline binding site, the assistance of Dr. Paul Ernsberger (Case Western Reserve University, Cleveland, Ohio) was enlisted, who performed phenylglyoxal attack of arginine on native PC-12 membranes. Dr. Ernsberger was able to demonstrate that this treatment completely eliminated imidazoline binding sites in these membranes. This provided indirect evidence that the native imidazoline binding site also contains an Arg residue. Attempts to chemically modify cysteine and tyrosine residues, which are not located near the Glu/Asp-rich region did not affect PC-12 membrane binding.

As a further test of the sequence, it was determined whether native IR$_1$ binding sites in PC-12 cells would be sensitive to ruthenium red. Inasmuch as the cloned sequence had suggested a similarity with the ryanodine receptor in terms of ruthenium red binding, it was reasoned that native IR$_1$ should bind ruthenium red. Accordingly, a competition of ruthenium red with $^{125}$PIC at PC-12 IR$_1$ sites was studied. In these studies it was observed that ruthenium red competed for $^{125}$PIC binding equally well as did the potent imidazoline compound, moxonidine, i.e., 100% competition. Furthermore, the IC$_{50}$ for competition of ruthenium red at IR$_1$ was more robust than has been previously reported for ruthenium red on the activation of calcium-dependent cyclic nucleotide phosphodiesterase—indicating that it might have pharmacological importance. It is also noteworthy that calcium failed to compete for $^{125}$PIC binding at PC-12 IR$_1$ sites (as did a calcium substitute, lanthanum). We have previously reported that a number of other cations robustly interfere with IR$_1$ binding [Ernsberger et al., *Annals NY Acad.Sci.*, 763: 22–42 (1995); Ernsberger et al., *Annals NY Acad.Sci.*, 763: 163–168 (1995)]. Attempts were also made to directly stain the proteins in SDS gels with ruthenium red, and it was found that ruthenium red stains the same platelet (33 kDa) and brain (85 kDa) bands that Reis antiserum detects. That 33 kDa band was verified to directly correlate with $^{125}$PIC Bmax values for IR$_1$. Thus, these results strongly link the attributes predicted from the cloned sequence to a native IR$_1$ binding site.

Some additional findings about the amino acid sequence of an instant IR$_1$ polypeptide are: (1) it bears a similarity to an amino acid sequence within a GTPase activator protein; (2) it contains at least seven small hydrophobic domains indicative of seven transmembrane domain receptors; and (3) three potential protein kinase C (PKC) phosphorylation sites are near to the carboxy terminus, and we have previously found that treatment of membranes with PKC leads to an enhancement of native IR$_1$ binding. Thus, these observations are all consistent with the observations previously expected for IR$_1$.

Northern blotting has also been performed on polyA+ mRNA from 22 human tissues in order to ascertain the regional expression of the mRNA corresponding to our cDNA. For these studies, a carboxy terminal coding sequence of clone 5A-1 (minus the Glu/Asp-rich region) was used as the labelled probe. This region was not found on any other known sequences on the BLASTN database. The results revealed a 6 kb mRNA band, which predominated over a much fainter 9.5 kb mRNA in most regions. The two exceptions to this pattern were in lymph nodes and cerebellum, where the 9.5 kb band was equally or more intense. In either case, the size of these mRNAs could easily encode a 70 kDa protein. Although the 6 kb band is weakly detectable in some non-CNS tissues, it is strikingly enriched in brain. An enrichment of the 6 kb mRNA is observed in brainstem, although not exclusively. Importantly, the regional distribution of the MRNA is generally in keeping with the known distribution of IR$_1$ binding sites, when extrapolated across species. Thus, the rank order of Bmax values for IR$_1$ in rat brain has been reported to be frontal cortex>hippocampus>medulla oblongata>cerebellum [Kamisaki et al., *Brain Res.*, 514: 15–21 (1990)]. Therefore, with the exception of human cerebellum, which showed two mRNA bands, the distribution of the mRNA for the present cloned cDNA is consistent with it belonging to IR$_1$.

It should be noted that while IR$_1$ binding sites are widely considered to be low in cerebral cortex compared to brainstem, this is in fact a misinterpretation of the literature based only on comparisons to the alpha-2 adrenoceptor's Bmax, rather than on absolute values. Thus, IR$_1$ Bmax values have actually been reported to be slightly higher in the cortex than the brainstem, but they "appear" to be low in the cortex in comparison to the abundance of alpha-2 binding sites in cortex. Therefore, the distribution of the IR$_1$ mRNA is very much in keeping with the actual Bmax values for radioligand binding to the receptor [Kamisaki et al., (1990)].

Conclusion

A DNA molecule of the present invention expresses a protein that is immunoreactive with both of the known selective antisera for an imidazoline receptor, i.e., Reis antiserum and Dontenwill antiserum. Thus, an instant cDNA molecule produces a protein immunologically related to a purified imidazoline receptor and has the antigenic specificity expected for an imidazoline binding site. These antisera have been documented in the scientific literature as being selective for an "imidazoline receptor", which provides strong evidence that such an imidazoline receptor has indeed been cloned.

An instant cDNA sequence contains an open reading frame for a 70 kDa protein distinct from any previously described proteins having affinity for imidazoline compounds, i.e., the protein is not an $\alpha_2$-adrenoceptor or monoamine oxidase. Also, at least seven small hydrophobic domains in the amino acid sequence corresponding to the DNA sequence have been identified, which suggests that the protein is probably membrane bound, as is expected for an imidazoline receptor. A short sequence homology was also observed with a domain in the human ryanodine receptor that encodes the ruthenium red binding site in the ryanodine receptor.

Further evidence that an IR$_1$ cDNA has been cloned is apparent from the fact that native IR$_1$ binding sites in PC-12 cells were found to be inhibited by ruthenium red dye. Moreover, ruthenium red was found to stain the protein band previously identified by us as the IR$_1$ protein in human platelets [Chen and MacLennan, *J. Biol. Chem.*, 269: 22698–22704 (1994)]. Thus, based solely on our sequence we were able to predict that native imidazoline receptors would possess ruthenium red binding capacity, a finding that further establishes that an imidazoline receptor has indeed been cloned. A summary of this evidence that a cDNA encoding an imidazoline receptor (probably IR$_1$) protein has been cloned is summarized in the Table hereinbelow.

TABLE

Comparison of Properties of cDNA Clone with Properties of IR$_1$ and I$_2$ Sites

| Imidazoline Receptor-like Clone | Authentic IR$_1$ | Authentic I$_2$ |
|---|---|---|
| λ phage fusion protein is immunoreactive with Dontenwill and Reis antibodies | Dontenwill Ab inhibits RVLM IR$_1$ binding site ($^3$H-CLON) Reis Ab immunoreactivity correlates with platelet IR$_1$ Bmax ($^{125}$PIC). | Dontenwill & Reis Abs both inhibit brain I$_2$ site ($^3$H-IDX). |
| No G-Protein-binding consensus sequence; but similar to a GTPase activator protein | Weak-to-moderate sensitivity to GTP | Not sensitive to GTP |
| Predicts 70,000 MW protein | 85,000 MW immunoreactivity | 59–61,000 MW photoaffinity |

TABLE-continued

Comparison of Properties of cDNA Clone with Properties of $IR_1$ and $I_2$ Sites

| Imidazoline Receptor-like Clone | Authentic $IR_1$ | Authentic $I_2$ |
| --- | --- | --- |
| Predicts 7 hydrophobic domains | Enriched in plasma membranes | Enriched in mitochondria |
| Encodes Glu/Asp-rich (negatively charged) domain consistent with $Ca^{++}$ and ruthenium red binding | ● Binds (+)-charged imidazolines<br>● Sensitive to divalent cations<br>● Sensitive to ruthenium red | ● Binds (+)-charged imidazolines<br>● Not sensitive to divalent cations<br>● Unknown sensitivity for Ru red |
| Arginine is only positively charged amino acid near Glu/Asp domain | ● Arg attack eliminates binding<br>● Cys & Tyr attack w/o effect | Unknown |
| Encodes PKC sites | PKC treatment enhances binding | Unknown |
| Human mRNA Distribution; F.Cortex > hippocampus > medulla | Rat $IR_1$ Bmax ($^{125}$PIC): F.Cortex > hippocampus > medulla | Rat $I_2$ Bmax ($^3$H-IDX): Medulla > F. Cortex |
| Transfected COS-7 cells have high affinity for moxonidine & p-iodoclonidine (PIC) | High affinity for moxonidine and PIC | Low affinity for moxonidine and PIC |

EXAMPLE 3

Transfection Studies

Figure 3:
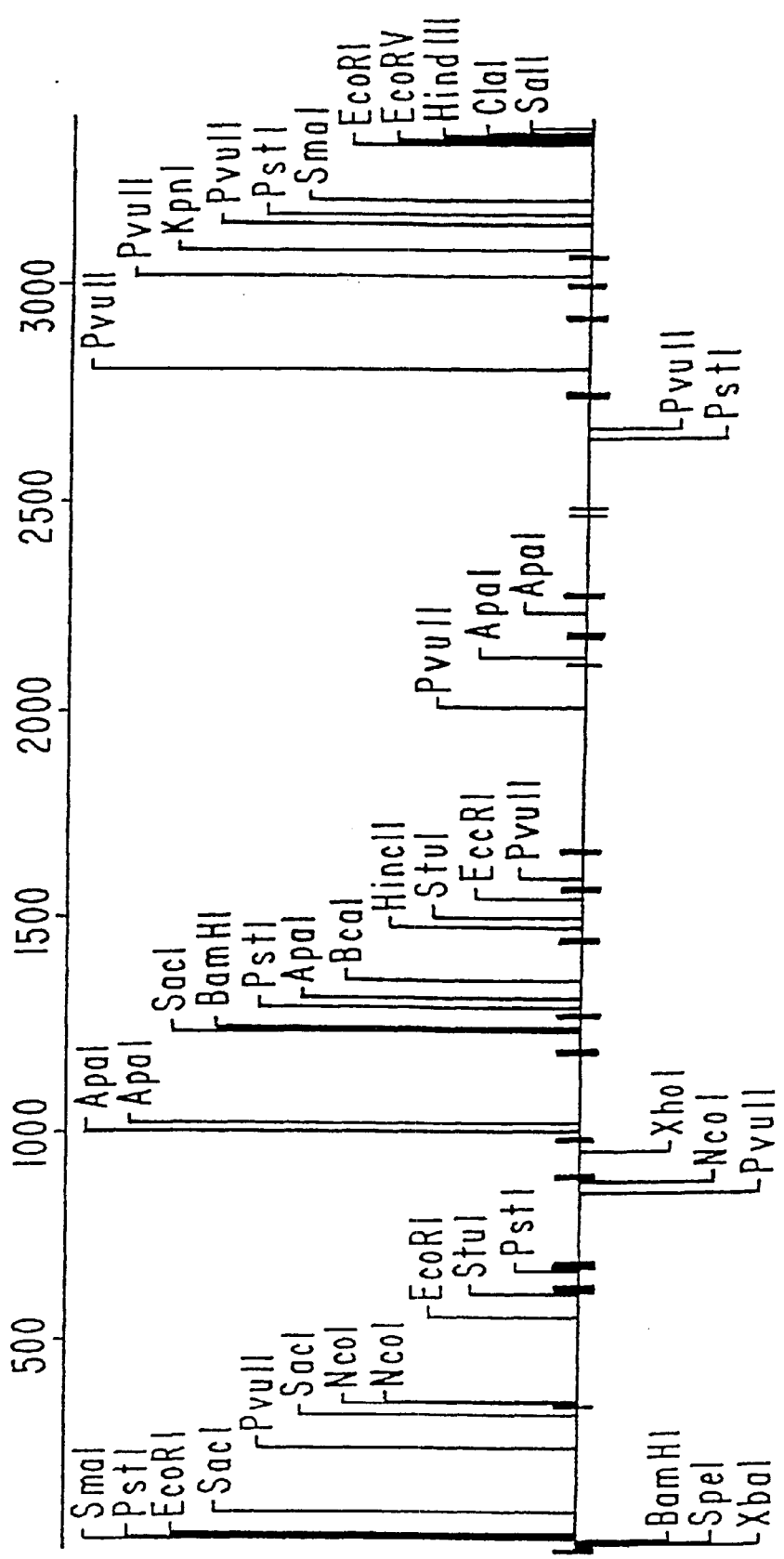
FIG. 3 depicts the restriction map of the IR$_1$ cDNA clone.

Transient transfection studies using the above-described full length EST04033 cDNA have been performed. COS-7 cells were transfected with a vector containing the EST04033 cDNA, which was predicted based on sequence analysis to contain the entire coding region of the imidazoline receptor protein, lacking only some 5' and 3' untranslated sequences. The EST04033 cDNA was subcloned into pSVK3 (Pharmacia LKB Biotechnology, Piscataway, N.J.) using standard techniques [Sambrook, supra], and trarisfected via the DEAE-dextran technique as previously described [Choudhary et al., *Mol.Pharmacol.*, 42: 627–633 (1992); Choudhary et al., *Mol.Pharmacol.*, 43: 557–561 (1993); Kohen et al., *J.Neurochem.*, 66: 47–56 (1996)]. A restriction map of the EST04033 cDNA is shown in FIG. 3. The restriction enzymes Sal I and Xba I were used for subcloning into pSVK3.

Briefly stated, COS-7 cells were seeded at $3 \times 10^6$ cells/100 mm plate, grown overnight and exposed to 2 ml of DEAE-dextran/plasmid mixture. After a 10–15 min. exposure, 20 ml of complete medium (10% fetal calf serum; 5 μg/ml streptomycin; 100 units/ml penicillin, high glucose, Dulbeccos' modified Eagle's medium) containing 80 μM chloroquine was added and the incubation continued for 2.5 hr. at 37° C. in a 5% $CO_2$ incubator. The mixture was then aspirated and 10 ml of complete medium containing 10% dimethyl sulfoxide was added with shaking for 150 seconds.

Following aspiration, 15 ml of complete medium with dialyzed serum was added and the incubation continued for an additional 65 hours. After this time period, the cells from 6 plates were harvested and membranes were prepared as previously described [Ernsberger et al., *Annals NY Acad. Sci.*, 763: 22–42 (1995), the disclosure of which is incorporated herein by reference]. Parent, untransfected COS-7 cells were prepared as a negative control. Some membranes were treated with and without PKC for 2 hrs prior to analysis, since previous studies had indicated that receptor phosphorylation could be beneficial to detect $IR_1$ binding.

The protocol used for Western blot assay of transfected cells is as follows. Cell membranes are prepared in a special cocktail of protease inhibitors (1 mM EDTA, 0.1 mM EGTA, 1 mM phenylmethyl-sufonylfluoride, 10 mM ε-aminocaproic acid, 0.1 mM benzamide, 0.1 mM benzamide-HCl, 0.1 mM phenanthroline, 10 μg/ml pepstatin A, 5 mM iodoacetamide, 10 μg/ml antipain, 10 μg/ml trypsin-chymotrypsin inhibitor, 10 μg/ml leupeptin, and 1.67 μg/ml calpain inhibitor) in 0.25 M sucrose, 1 mM $MgCl_2$, 5 mM Tris, pH 7.4. Fifteen μg of total protein are denatured and separated by SDS gel electrophoresis. Gels are equilibrated and electrotransferred to nitrocellulose membranes. Blots are then blocked with 10% milk in Tris-buffered saline with 0.1% Tween-20 (TBST) during 60 min. of gentle rocking. Afterwards, blots are incubated in anti-imidazoline receptor antiserum (1:3000 dil.) for 2 hours. Following the primary antibody, blots are washed and incubated with horseradish peroxidase-conjugated anti-rabbit goat IgG (1:3000 dil.) for 1 hr. Blots are extensively washed and incubated for 1 min. in a 1:1 mix of Amersham ECL detection solution. The blots are wrapped in cling-film (SARAN WRAP) and exposed to Hyperfilm-ECL (Amersham) for 2 minutes. Quantitation was based on densitometry using a standard curve of known amounts of protein containing BAC membranes or platelet membranes run in each gel.

One nM [$^{125}$I]p-iodoclonidine was employed as radioligand in the competition assays, since at this low concentration this radioligand is selective for the $IR_1$ site much more than for $I_2$ binding sites. The critical processes of membrane preparation of tissue culture cells and the radioligand binding assays of $IR_1$ and $I_2$ have recently been reviewed by Piletz and colleagues [Ernsberger et al., *Annals NY Acad Sci.*, 763: 510–519 (1995)]. Total binding (n=12 per experiment) was determined in the absence of added competitive ligands and nonspecific binding was determined in the presence of $10^{-4}$ M moxonidine (n=6 per experiment). Log normal competition curves were generated against unlabeled moxonidine, p-iodoclonidine, and (−) epinephrine. Each concentration of the competitors was determined in triplicate and the experiment was repeated thrice.

The protocol to fully characterize radioligand binding in the transfected cells entails the following. First, the presence of $IR_1$ and/or $I_2$ binding sites are scanned over a range of protein concentrations using a single concentration of [$^{125}$I]-p-iodoclonidine (1.0 nM) and $^3$H-idazoxan (8 nM), respectively. Then, rate of association binding experiments (under a 10 μM mask of NE to remove $\alpha_2$AR interference) are performed to determine if the kinetic parameters are similar to those reported for native imidazoline receptors [Ernsberger et al. *Annals NY Acad. Sci.*, 763: 163–168 (1995)]. Then, full Scatchard plots of [$^{125}$I]-p-iodoclonidine (2–20 nM if like $IR_1$) and $^3$H-idazoxan (5–60 nM if like $I_2$) binding are conducted under a 10 μM mask of NE. Total NE (10 μM)-displaceable binding is ascertained as a control to rule out $\alpha_2$-adrenergic binding. The Bmax and $K_D$ parameters for the transfected cells are ascertained by computer modeling using the LIGAND program [McPherson, G., *J.Pharmacol.Meth.*, 14: 213–228 (1985)] using 20 μM moxonidine to define $IR_1$ nonspecific binding, or 20 μM cirazoline to define $I_2$ nonspecific binding.

Figure 4:
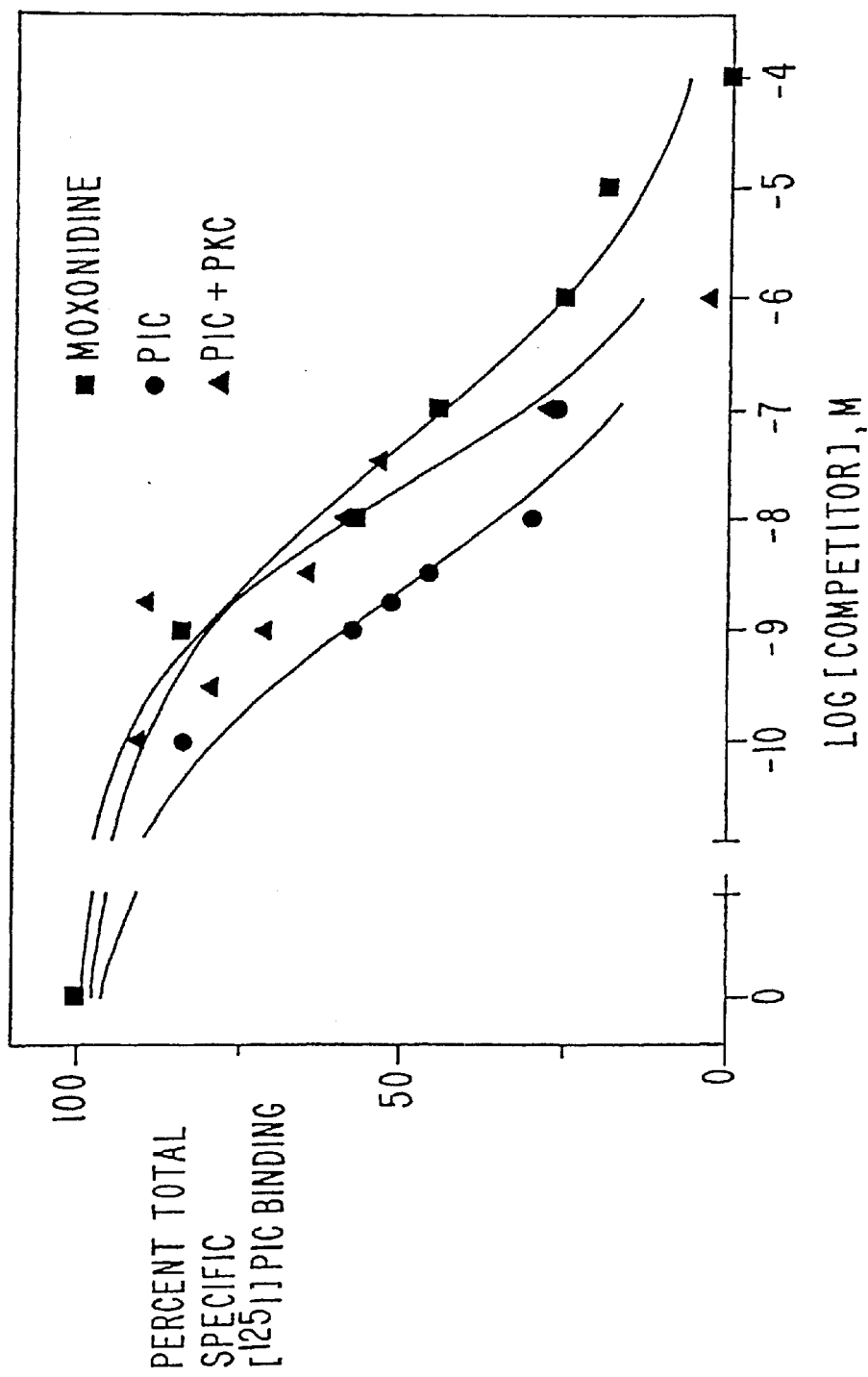
FIG. 4 depicts a competitive binding assay between $^{125}$I-labelled p-iodoclonidine (PIC) and various ligands for the imidazoline receptor on membranes expressed in COS cells transfected with the $IR_1$ cDNA clone, as discussed in Example 3.

The results of the transient transfection experiments of the imidazoline receptor vector into COS-7 cells are shown in FIG. 4. Competition binding experiments were performed using membrane preparations from these cells and $^{125}$PIC was used to radiolabel I-sites. A mask of 10 μM norepinephrine was used to rule out any possible $\alpha_2$AR binding in each assay even though parent COS-7 cells lacked any $\alpha_2$AR sites. Moxonidine and p-iodoclondine (PIC) were the compounds tested for their affinity to the membranes of transfected cells. As can be seen, the affinities of these compounds in competition with $^{125}$PIC were well within the high affinity (nM) range. The following $IC_{50}$ values and Hill slopes were obtained in this study: moxonidine, $IC_{50}$=45.1 nM (Hill slope=0.35±0.04); p-iodoclonidine without PKC pretreatment, $IC_{50}$=2.3 nM (Hill slope=0.42±0.06); p-iodoclonidine with PKC pretreatment, $IC_{50}$=19.0 nM (Hill slope=0.48±0.08). Shallow Hill slopes for $[^{125}I]$p-iodoclonidine have been reported before in studies of the interaction of moxonidine and p-iodoclonidine with the human platelet $IR_1$ binding site [Piletz and Sletten, (1993)]. Epinephrine failed to displace any of the $[^{125}I]$p-iodoclonidine binding in the transfected cells, as expected since this is a nonadrenergic imidazoline receptor. Furthermore, in untransfected cells less than 5% of the amount of displaceable binding was observed as for the transfected cells—and this "noise" in the parent cells all appeared to be low affinity (data not shown). These results thus demonstrate the high affinities of two imidazoline compounds, p-iodoclonidine and moxonidine for our cloned receptor. PKC pretreatment had no effect in the transfected COS cells.

It was also observed that the level of the expressed protein, as measured by immunoblotting of the transfected cells, was consistent with the level of $IR_1$ binding that was detected. Hence, the present results are in keeping with those expected for the native imidazoline receptor. In summary, these data provide direct evidence that the EST04033 clone encodes an imidazoline binding site having high affinities for moxonidine and p-iodoclonidine, which is expected for the $IR_1$ protein.

EXAMPLE 4

Stable Transfection Methods

Stable transfections can be obtained by subcloning the imidazoline receptor cDNA into a suitable expression vector, e.g., pRc/CMV (Invitrogen, San Diego, Calif.), which can then be used to transform host cells, e.g. CHO and HEK-293 cells, using the Lipofectin reagent (Gibco/BRL, Gaithersburg, Md.) according to the manufacturer's instructions. These two host cell lines can be used to increase the permanence of expression of an instant clone. The inventors have previously ascertained that parent CHO cells lack both alpha$_2$-adrenoceptor and $IR_1$ binding sites [Piletz et al., *J. Pharm. & Exper. Ther.*, 272: 581–587 (1995)], making them-useful for these studies. Twenty-four hours after transfection, cells are split into culture dishes and grown in the presence of 600 μg/ml G418-supplemented complete medium (Gibco/BRL). The medium is changed every 3 days and clones surviving in G418 are isolated and expanded for further investigation.

EXAMPLE 5

Direct Cloning of Human Genomic $IR_1$

Direct cloning from a human genomic library can be done by preparing labelled cDNA probes from different subcloned regions of our full-length cDNA and using the probes to screen a commercially available human brain genomic library. One genomic library is EMBL (Clontech), which integrates genomic fragments up to 22 kbp long. It is reasonable to expect that introns may exist within the human gene so that only by obtaining overlapping clones can the full gene be sequenced. A probe encompassing the 5' end of an instant cDNA is generally useful to obtain the gene promoter region. Clontech's Human PromoterFinder DNA Walking procedure provides a method for "walking" upstream or downstream from cloned sequences such as cDNAs into adjacent genomic DNA.

EXAMPLE 6

Methods for Preparing Antibodies to Imidazoline Receptive Proteins

An instant imidazoline receptive polypeptide can also be used to prepare antibodies immunoreactive therewith. Thus, transfected cell lines or other manipulations of the DNA sequence of an instant imidazoline receptor can provide a source of purified imidazoline receptor protein in sufficient quantities for immunization, which can lead to a source of selective antibodies having commercial value.

In addition, various kits for assaying imidazoline receptors can be developed that include either such antibodies or the purified imidazoline receptor protein. A purification protocol has already been published for the bovine imidazoline receptor in BAC cells [Wang et al, 1992] and an immunization protocol has also been published [Wang et al., 1993]. These same protocols can be utilized with little if any modification to afford purified human $IR_1$ protein and selective antibodies thereto.

In order to obtain antibodies to a subject peptide, the peptide may be linked to a suitable soluble carrier to which antibodies are unlikely to be encountered in human serum. Illustrative carriers include bovine serum albumin, keyhole limpet hemocyanin, and the like. The conjugated peptide is injected into a mouse, or other suitable animal, where an immune response is elicited. Monoclonal antibodies can be obtained from hybridomas formed by fusing spleen cells harvested from the animal and myeloma cells [see, e.g., Kohler and Milstein, *Nature*, 256: 495–497 (1975)].

Once an antibody is prepared (either polyclonal or monoclonal), procedures are well established in the literature, using other proteins, to develop either RIA or ELISA assays for imidazoline receptive protein [see, e.g., "Radioimmunoassay of Gut Regulatory Peptides; Methods in Laboratory Medicine," Vol. 2, chapters 1 and 2, Praeger Scientific Press, 1982]. In the case of RIA, the purified protein can also be radiolabelled and used as a radioactive antigen tracer.

Currently available methods to assay imidazoline receptors are unsuitable for routine clinical use, and therefore the development of an assay kit in this manner would have significant market appeal. Suitable assay techniques can employ polyclonal or monoclonal antibodies, as has been previously described [U.S. Pat. No. 4,376,110 (issued to David et al.), the disclosure of which is incorporated herein by reference].

Summary

In summary, we have identified a unique cDNA sequence and have shown that it has the properties expected of an imidazoline receptor. Although two partial sequences of the entire sequence were found in public databases on the Internet, these are partial sequences (155–250 bp) and were not identified at all with respect to any encoded protein. Moreover, neither of these sequences reliably defines any portion of the coding region for an instant $IR_1$ protein. The EST04033 clone, which was reported to contain the 155 bp sequence, was sequenced for the first time by the present inventors in its entirety (3318 bp) by the inventors. Prior to this, even the size of EST04033 was unknown. The present inventors also demonstrated that an imidazoline receptive site can be expressed in cells transfected with the entire cDNA clone, and this site has the proper potencies for an $IR_1$. Thus, a DNA sequence with an open reading frame for a 70 kDa human $IR_1$ protein has been identified from our clones and the amino acid sequence of the protein has been deduced. The authenticity of the expressed protein as that defining an $IR_1$ protein has been demonstrated in a variety of ways.

The present invention has been described with reference to specific examples for purposes of clarity and explanation. Certain obvious modifications of the invention readily apparent to one skilled in the art can be practiced within the scope of the appended claims.

What is claimed is:

1. An isolated polypeptide comprising the amino acid sequence shown in SEQ ID NO:7.

2. The polypeptide of claim 1, wherein said polypeptide has the ability to bind to at least one of p-iodoclonidine and moxonidine.

3. The polypeptide of claim 1, wherein said polypeptide is immunoreactive with at least one of Reis antiserum and Dontenwill antiserum.

4. The polypeptide of claim 1 having a molecular weight of about 60 to 80 kDa.

5. The polypeptide of claim 4 having a molecular weight of about 70 kDa.

6. The polypeptide of claim 1 having a molecular weight of about 35 to 45 kDa.

7. The polypeptide of claim 6 having a molecular weight of about 37 kDa.

8. An isolated polypeptide that is receptive to imidazoline compounds, said polypeptide being produced by expression of a polynucleotide comprising the nucleotide sequence shown in SEQ ID NO: 1, 2, 3, or 4 operably linked with a promoter sequence, or a polynucleotide which hybridizes under stringent conditions with at least one of said nucleotide sequence, wherein said stringent conditions comprise 0.1×SSC, 0.5% SDS at 65° C.

* * * * *